(12) United States Patent
Insley et al.

(10) Patent No.: US 6,290,685 B1
(45) Date of Patent: Sep. 18, 2001

(54) MICROCHANNELED ACTIVE FLUID TRANSPORT DEVICES

(75) Inventors: Thomas I. Insley, West Lakeland Township; Raymond P. Johnston, Lake Elmo; Randall L. Knoll, Stillwater, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/099,269

(22) Filed: Jun. 18, 1998

(51) Int. Cl.[7] .............................. A61M 1/100; F23L 15/02
(52) U.S. Cl. ...................... 604/317; 604/322; 604/319; 165/6
(58) Field of Search ..................... 604/317, 322, 604/319, 19, 268, 27, 28, 289–290, 30, 312–314, 316, 32–35, 323, 326, 356–357, 73, 902; 165/6; 128/134, 303 R, 846–847, 849–852; 15/310–311; 204/195 B, 195 M, 195 R; 210/488–490, 492, 496, 498, 500, 506; 23/230 B, 230 R; 269/15, 21, 327, 244; 422/100, 68, 79; 435/310, 4; 442/50–58

(56) References Cited

U.S. PATENT DOCUMENTS

| | | |
|---|---|---|
| 1,555,574 | 9/1925 | Herrmann . |
| 1,646,404 | 10/1927 | Herbert . |
| 3,037,633 | 6/1962 | Veitel et al. . |
| 3,234,639 | 2/1966 | Dietzsch . |
| 3,511,381 | 5/1970 | Alwall et al. . |

(List continued on next page.)

FOREIGN PATENT DOCUMENTS

| | | |
|---|---|---|
| 32 12 295 A1 | 10/1983 | (DE) . |
| 42 10 072 A1 | 3/1993 | (DE) . |
| 195 01 017 A1 | 7/1996 | (DE) . |
| 195 41 266 A1 | 5/1997 | (DE) ............................ B01J/10/00 |
| 0 039 291 A1 | 11/1981 | (EP) . |

(List continued on next page.)

OTHER PUBLICATIONS

Article: "Fabrication of Novel Three–Dimensional Microstructures by the Anisotropic Etching of (100) and (110) Silicon", Ernest Bassous, *IEEE Transactions on Electron Devices*, vol. ED–25, No. 10, Oct. 1978.

Article: "Simple and Low Cost Fabrication of Embedded Micro–Channels by Using a New Thick–Film Photoplastic" Guerin, et al. *Digest of Technical Papers*, vol. 2, Jun. 1997.

Article: "Fabrication of Microstructures with high aspect ratios and great structural heights by synchrotron radition lithography, galvanoforming, and plastic moulding (LIGA process)" Becker, et al. *MiMicroelectronic Engineering* 4 (1986).

Article: "For lab chips, the future is plastic". IVD Technology Magazine, May 1997.

(List continued on next page.)

Primary Examiner—Glenn K. Dawson
Assistant Examiner—Jamisue A. Webb

(57) ABSTRACT

An active fluid transport device (10, 40, 54, 60) that includes a layer (12) of polymeric material. The layer (12) has a structured surface (13) that includes a plurality of substantially discrete flow channels (16). The flow channels (16) have a minimum aspect ratio of about 10 to 1 and a hydraulic radius no greater than about 300 micrometers. The device may also include a connector (20, 55) that allows a potential source (14) external to the structured surface (13) to be placed in fluid communication with the discrete flow channels (16). The potential source (14) promotes fluid movement through the flow channels (16) from a first location to a second location.

103 Claims, 4 Drawing Sheets

U.S. PATENT DOCUMENTS

| | | |
|---|---|---|
| 3,520,300 | 7/1970 | Flower, Jr. .......................... 128/276 |
| 3,598,127 | 8/1971 | Wepsic . |
| 3,715,192 | 2/1973 | Wenz et al. . |
| 3,812,972 | 5/1974 | Rosenblum . |
| 3,921,627 | 11/1975 | Wilson et al. . |
| 3,935,863 | 2/1976 | Kliger . |
| 3,993,566 | 11/1976 | Goldberg et al. .............. 210/433 M |
| 4,186,745 | 2/1980 | Lewis et al. . |
| 4,233,029 | 11/1980 | Columbus . |
| 4,271,119 | 6/1981 | Columbus . |
| 4,277,966 | 7/1981 | Rambauske . |
| 4,323,069 | 4/1982 | Ahr et al. . |
| 4,392,362 | 7/1983 | Little ................................. 62/514 R |
| 4,413,407 | 11/1983 | Columbus ............................. 29/825 |
| 4,525,166 | 6/1985 | Leclerc . |
| 4,533,352 | 8/1985 | Van Beek et al. ................... 604/317 |
| 4,579,555 | 4/1986 | Russo . |
| 4,601,861 | 7/1986 | Pricone et al. ........................ 264/1.6 |
| 4,623,329 | 11/1986 | Drobish et al. . |
| 4,639,748 | 1/1987 | Drake et al. ..................... 346/140 R |
| 4,668,558 | 5/1987 | Barber . |
| 4,677,705 | 7/1987 | Schuster ............................... 15/398 |
| 4,679,590 | 7/1987 | Hergenroeder . |
| 4,686,041 | 8/1987 | Van den Berg et al. . |
| 4,725,270 | 2/1988 | Schuldt et al. . |
| 4,726,900 | 2/1988 | Keskinen et al. . |
| 4,747,166 | 5/1988 | Kuntz . |
| 4,751,000 | 6/1988 | Drori . |
| 4,758,481 | 7/1988 | Fauvel . |
| 4,867,747 | 9/1989 | Yarger . |
| 4,867,876 | 9/1989 | Kopf . |
| 4,871,623 | 10/1989 | Hoopman et al. . |
| 4,890,628 | 1/1990 | Jackson . |
| 4,906,439 | 3/1990 | Grenner ................................. 422/56 |
| 4,913,858 | 4/1990 | Miekka et al. ........................ 264/1.3 |
| 4,921,492 | 5/1990 | Schultz et al. . |
| 4,950,549 | 8/1990 | Rolando et al. . |
| 4,966,584 | 10/1990 | Nguyen . |
| 4,978,450 | 12/1990 | Drori . |
| 5,014,389 | 5/1991 | Ogilvie et al. ........................ 15/353 |
| 5,037,548 | 8/1991 | Rosenberg . |
| 5,042,978 | 8/1991 | Quenin et al. . |
| 5,045,075 | 9/1991 | Ersek . |
| 5,055,188 | 10/1991 | Nagoshi et al. . |
| 5,057,710 | 10/1991 | Nishiura et al. . |
| 5,069,403 | 12/1991 | Marentic et al. . |
| 5,070,606 | 12/1991 | Hoopman et al. . |
| 5,078,925 | 1/1992 | Rolando et al. . |
| 5,112,503 | 5/1992 | Raifman . |
| 5,126,022 | 6/1992 | Soane et al. . |
| 5,133,516 | 7/1992 | Marentic et al. . |
| 5,152,060 | 10/1992 | Schubert et al. ................ 29/890.039 |
| 5,158,557 | 10/1992 | Noreen et al. . |
| 5,161,544 | 11/1992 | Morris . |
| 5,171,307 | 12/1992 | Sanning . |
| 5,175,030 | 12/1992 | Lu et al. . |
| 5,176,667 | 1/1993 | DeBring ............................... 604/356 |
| 5,200,248 | 4/1993 | Thompson et al. . |
| 5,205,348 | 4/1993 | Tousignant et al. . |
| 5,249,358 | 10/1993 | Tousignant et al. . |
| 5,249,359 | 10/1993 | Schubert et al. . |
| 5,268,213 | 12/1993 | Murakami et al. . |
| 5,296,375 | 3/1994 | Kricka et al. . |
| 5,304,487 | 4/1994 | Wilding et al. . |
| 5,314,743 | 5/1994 | Meirowitz et al. . |
| 5,317,805 | 6/1994 | Hoopman et al. . |
| 5,345,946 | 9/1994 | Butterworth et al. . |
| 5,349,965 | 9/1994 | McCarver . |
| 5,368,910 | 11/1994 | Langdon . |
| 5,376,252 | 12/1994 | Ekstrom et al. . |
| 5,395,315 | 3/1995 | Griep . |
| 5,411,858 | 5/1995 | McGeehan et al. ..................... 435/4 |
| 5,429,807 | 7/1995 | Matson et al. . |
| 5,434,339 | 7/1995 | La Motte et al. . |
| 5,437,651 | 8/1995 | Todd et al. ........................... 604/313 |
| 5,440,332 | 8/1995 | Good . |
| 5,445,771 | 8/1995 | Dengen . |
| 5,445,934 | 8/1995 | Fodor et al. . |
| 5,450,235 | 9/1995 | Smith et al. . |
| 5,457,848 | 10/1995 | Miwa ..................................... 15/346 |
| 5,474,796 | 12/1995 | Brennan . |
| 5,498,392 | 3/1996 | Wilding et al. . |
| 5,500,071 | 3/1996 | Kaltenbach et al. . |
| 5,514,120 | 5/1996 | Johnston et al. . |
| 5,527,588 | 6/1996 | Camarda et al. . |
| 5,534,576 | 7/1996 | Grot ..................................... 524/377 |
| 5,536,699 | 7/1996 | Ghelfi et al. . |
| 5,571,410 | 11/1996 | Swedberg et al. . |
| 5,599,330 | 2/1997 | Rainin . |
| 5,601,678 | 2/1997 | Gerber et al. ........................ 156/150 |
| 5,614,093 | 3/1997 | Mueggenburg et al. . |
| 5,628,735 | 5/1997 | Skow ................................... 604/317 |
| 5,635,358 | 6/1997 | Wilding et al. . |
| 5,637,469 | 6/1997 | Wilding et al. . |
| 5,641,400 | 6/1997 | Kaltenbach et al. . |
| 5,645,702 | 7/1997 | Witt et al. . |
| 5,651,888 | 7/1997 | Shimizu et al. ................. 210/321.64 |
| 5,651,900 | 7/1997 | Keller et al. . |
| 5,655,258 | 8/1997 | Heintz . |
| 5,658,413 | 8/1997 | Kaltenbach et al. . |
| 5,658,802 | 8/1997 | Hayes et al. . |
| 5,691,846 | 11/1997 | Benson, Jr. et al. .................. 359/530 |
| 5,692,263 | 12/1997 | Sorenson ............................ 15/415.1 |
| 5,698,299 | 12/1997 | Schmidt et al. . |
| 5,703,633 | 12/1997 | Gehrer et al. .......................... 347/86 |
| 5,705,813 | 1/1998 | Apffel et al. . |
| 5,707,799 | 1/1998 | Hansmann et al. . |
| 5,716,825 | 2/1998 | Hancock et al. . |
| 5,726,026 | 3/1998 | Wilding et al. . |
| 5,728,446 | 3/1998 | Johnston et al. . |
| 5,750,015 | 5/1998 | Soane et al. . |
| 5,755,942 | 5/1998 | Zanzucchi et al. . |
| 5,757,482 | 5/1998 | Fuchs et al. . |
| 5,797,978 | 8/1998 | Rosenberg et al. . |
| 5,798,042 | 8/1998 | Chu et al. . |
| 5,842,787 | 12/1998 | Kopf-Sill et al. ..................... 366/340 |
| 5,885,470 | 3/1999 | Parce et al. ............................ 216/33 |
| 5,932,315 | 8/1999 | Lum et al. . |
| 5,952,173 | 9/1999 | Hansmann et al. . |

FOREIGN PATENT DOCUMENTS

| | | |
|---|---|---|
| 0 329 340 A2 | 8/1989 | (EP) . |
| 0 547 496 A1 | 12/1992 | (EP) . |
| 0 640 385 A1 | 8/1993 | (EP) . |
| 1 338 579 | 11/1973 | (GB) . |
| 1 354 502 | 5/1974 | (GB) . |
| 1 418 635 | 12/1975 | (GB) . |
| WO 89/04628 | 6/1989 | (WO) . |
| WO 93/11727 | 6/1993 | (WO) . |
| WO 96/04547 | 2/1996 | (WO) . |
| WO 96/10747 | 4/1996 | (WO) . |
| WO 97/02357 | 1/1997 | (WO) . |
| WO 97/13633 | 4/1997 | (WO) . |
| WO 98/00231 | 1/1998 | (WO) . |
| WO 98/24544 | 6/1998 | (WO) . |
| WO 98/46438 | 10/1998 | (WO) . |
| WO 99/06589 | 2/1999 | (WO) . |

OTHER PUBLICATIONS

Article: "UV Laser Machined Polymer Substrates for the Development of Microdiagnostic Systems" Roberts, et al. *Analytical Chemistry*, vol. 69, No. 11, Jun. 1997.

Article: "Microchannel Electrophoretic Separations of DNA in Injection–Molded Plastic Substrates" McCormick et al. *Analytical Chemistry*, vol. 69, No. 14, Jul. 1997.

Bier, W., et al., *Gas to Gas Heat Transfer In Micro Heat Exchangers,* Chemical Engineering and Processing, pp. 33–43 (1993).

Ottow, S., et al., *Processing of Three–Dimensional Microstructures Using Macroporous n–Type Silicon,* J. Electrochem. Soc., vol. 143, No. 1, pp. 385–390 (Jan. 1996).

Zuska, P., *Microtechnology Opens Doors to the Universe of Small Space*, Medical Device & Diagnostic Industry, pp. 131–137 (Jan. 1997).

Kernforschungszentrum Karlsruhe product literature for Metal Micro Heat Exchangers.

Tecnol product literature for Fluid Control Floor Suction Mat (1997).

Colby Manufacturing Corporation product literature for The Water Bug™.

Colby Manufacturing Corporation product literature for SurgiSafe (1995).

Davol product literature for ReliaVac® 100cc Closed Wound Suction Kits (1989).

Davol product literature for 100cc Silicone Evacuator (Jul. 1993).

Axiom Medical Inc. product literature for Clot–Stop™.

Axiom Medical Inc. Product Line Quick Reference Guide brochure.

Bio–medical Devices Intl., Inc. product literature for Reel Thing™.

MICROCHANNELED ACTIVE FLUID TRANSPORT DEVICES

This invention pertains to a device that has a structured polymeric surface that contains discrete microstructured channels for transporting fluid. The device also has a connector that fluidically connects the discrete microstructured channels to a potential source that promotes fluid transport through the channels. The invention also pertains to a method of transporting a fluid using such a device and to a variety of articles that employ such a device.

BACKGROUND

Fluid transport may be characterized based on the mechanism that causes flow within the device. When fluid transport pertains to a nonspontaneous fluid flow regime that, for the most part, is the result of a force external to the device, the fluid transport is considered "active". On the other hand, when the fluid transport pertains to a spontaneous flow regime that stems from a property inherent to the device, the fluid transport is considered "passive". A catheter is a well-known example of an active fluid transport device. Typically, catheters are connected to a vacuum source that draws liquid through the device. An example of a passive fluid transport device is an absorbent pad or sponge.

The design of an active fluid transport device depends largely on the specific application to which it is applied. In many cases, it is desirable to control the fluid flow path. In one sense, the fluid flow path can be controlled for the purpose of running a particular fluid near another object or fluid such as in a heat exchanger.

A heat exchanger that has discrete microchannels extending between first and second manifolds is described in U.S. Pat. No. 5,317,805 to Hoopman et al. This microchanneled heat exchanger is produced by materially depositing a shell—such as by electroplating or vapor depositing a metal—about a sacrificial core. Another microchanneled heat exchanger is described in U.S. Pat. No. 5,070,606 also to Hoopman et al., which is made by forming a plastic or ceramic body about an arrangement of fibers that are subsequently removed to leave microchannels within the formed body.

In another sense, a fluid flow path can be controlled to make the fluid flow according to specific flow characteristics. That is, fluid flow may be facilitated simply through a single conduit, between layers, or by way of multiple channels. Other examples include porous products that can be attached to a potential generating device that causes fluid flow through the porous product—see, for example, U.S. Pat. No. 5,599,330 to Rainin, U.S. Pat. No. 4,533,352 to Van Beck et al., and U.S. Pat. No. 3,935,863 to Kliger.

A fluid transport flow path may be defined by multiple channels that are employed to transport a liquid from a collection site to another location such as a storage receptacle. When using such devices quite often, the liquid mixes with gas and a two-phase flow results, sometimes as a turbulent mix of the liquid and gas. Depending on mix ratios and the velocity of the fluid stream, the liquid and gas can combine in undesirable flow patterns. Patterns known as froth, dispersed, and slug flow can sometimes detrimentally affect the fluids being conveyed, or such flow can affect the transport system and/or surrounding environment.

In froth flow, for instance, bubbles of gas are dispersed throughout the liquid, and intimate contact of the air and liquid could cause, as an example, accelerated oxidation of the liquid. In dispersed flow, nearly all the liquid is entrained as fine droplets in the gas. Aerosol droplets generated by this flow pattern could find their way into the local environment, thus creating a hazard depending on the nature of the liquid. An example might be in a surgical field where bio-contaminated fluids, aspirated for disposal, become aerosolized and enter into work environment when collection canisters are opened. In slug flow, a wave of liquid is picked up periodically by rapidly moving gas to form a frothy slug that passes along the system at a velocity greater than the average liquid velocity. In this type of flow, slugs can cause equipment vibration when impacting upon system components. The impact can place a high level of mechanical stress on the fluid, in addition to elements in the system such as fittings and bends. Violent fluid transport action also could possibly break down the cellular structure of stress sensitive fluids, such as blood that is being collected for reintroduction during surgical procedures.

Two-phase flow can also detrimentally impact the workplace by generating noise during the fluid transport. That is, noise is often created when a turbulent liquid mixture moves through the device. Noise pollution must be minimized in many environments, particularly where good communication is essential, such as in an operating room.

U.S. Pat. No. 4,966,584 to Nguyen describes an active fluid transport device that addresses noise concerns. Specifically, a suction aspirator is described that is used during surgical procedures. The device incorporates a valve assembly that controls flow through the device to reduce noise. The valve purportedly controls noise by regulating suction flow through the device.

Another active fluid transport device that is used in the medical field is a fluid recovery floor mat that is commercially available under the trade name "Fluid Control" floor suction mat, from Technol Medical Products Inc. This product uses both passive and active means to remove fluids that fall from a surgical site during a surgical procedure. The device has an absorbent mat that resides above a multitude of parallel channels. Holes are provided in the channel surfaces that interface with the absorbent mat so that fluid recovered by the mat can be drawn into the channels. The parallel channels are connected to a manifold that attaches to suction tubing. Thus, after fluid has accumulated on the mat, removal can be facilitated through the multiple channels by applying a vacuum. Because the recovered liquid can flow through the channels as a liquid/air mixture, the device has the potential to generate noise. That is, as fluid is pulled through the channels by the suction system, air can mix with the liquid to generate noise that can negatively affect the working environment.

U.S. Pat. No. 5,628,735 to Skow discloses an active fluid transport device that professes to gently and continuously remove unwanted fluid from an operating field during surgery. The device utilizes both passive and active fluid transport mechanisms to remove excess fluids during surgical procedures. It includes a flexible mat that has a high wicking property, and embedded in the mat is a flexible suction tube that is attached to a suction source and that removes fluid from the mat to prevent it from becoming saturated. The tube has one or more holes in it to allow the recovered fluid to flow from the mat into the tube. Because the device does not employ multiple discrete channels, it is not capable of distributing the suction effect amongst such channels, and the use of a tubing can restrict applications for the device.

Other active fluid transport products that are used to recover fluids are described in U.S. Pat. Nos. 5,437,651 to Todd et al. and 4,679,590 to Hergenroeder. In Todd et al., a medical suction apparatus is disclosed that is useful for collecting blood and other fluids that accumulate in a patient during surgical procedures. The apparatus includes an absorbent foam pad that is attached to a suction source via a flexible backing plate. The backing plate has channels that direct the recovered fluid toward an orifice. This apparatus is highly susceptible to generating noise because a liquid/air mixture would commonly be drawn through the apparatus.

Hergenroeder describes a receptacle for collecting fluid from the floor of an operating room. The device is described as being especially suitable for collecting irrigation fluids used in surgical procedures such as arthroscopic surgery on a joint, e.g., a knee. The receptacle is thin and generally flat and has a gridwork of small basins that form a collecting surface with drains through which the recovered fluid flows to channels formed between the receptacle and the floor. The channels direct the fluid to a common discharge port, which may be connected to a suction device. Because of the channel configuration, this device, like others described above, may easily create a two-phase liquid/air flow, which could generate significant noise pollution.

Other flexible tubing devices or catheters are described, for example, in U.S. Pat. Nos. 5,445,771 to Degen, 4,623,329 to Drobish et al., and 3,598,127 to Wepsic. In the Degen patent, a collection of hollow thermoplastic fiber strands are secured together and used in the way of a separatory device. The devices described in Drobish et al and Wepsic are directed to catheters that have a primary flow passage and one or more secondary flow passages disposed between tubing layers. The Drobish et al device includes a concentric secondary passage that has grooves formed within one of the defining surfaces for increasing surface area that is accessible to fluid passed within the secondary passage. In the Wepsic patent, plural secondary v-shaped grooves are arranged around a primary passage. The v-shaped grooves are enclosed by an outer tube that is permeable to an antibacterial substance.

SUMMARY OF THE INVENTION

The present invention provides an active fluid transport device that includes a layer of polymeric material that has a first major surface. The first major surface includes a structured surface that has a plurality of substantially discrete flow channels disposed thereon. The flow channels extend from a first point to a second point along the structured surface and have a minimum aspect ratio of about 10:1 and a hydraulic radius no greater than about 300 micrometers ($\mu$m). The transport device also includes a connector that is in fluid communication with the discrete flow channels. The connector allows a potential, from a source external to the structured polymeric surface, to be applied to the flow channels to promote fluid movement through the flow channels from a first potential to a second potential.

The present invention has a number of characteristics that impart numerous advantages into an active fluid transport device that embodies the invention. One particular characteristic is the use of a microstructured surface that is formed from a polymeric material. The polymeric material allows the structured surface to be accurately replicated in a relatively inexpensive manner during manufacture. The polymeric layer that bears the microstructured surface can be readily replicated using a molding or casting technique. The structured surface thus can be produced without costly processing conditions that would otherwise be entailed when using other techniques such as machining and chemical etching. The use of polymeric materials for forming the microstructured surface also can allow individual feature fidelities to be maintained in the manufacturing process at relatively high tolerances. Additionally, the polymeric material enables flexible active fluid transport devices to be produced by selecting polymers that have a low tensile modulus. Articles using such polymers may be conformed into a variety of configurations for various utilities.

The provision of discrete flow channels that have a minimum aspect ratio of about 10:1 and a hydraulic radius of no greater than about 300 $\mu$m affords microstructured channels that allow the effect of the potential to be divided amongst numerous channels in a highly distributed manner. Rather than have the potential's total effect transmitted through, for example, a single large channel, the potential can be distributed among a very large number of small channels such that no one channel could adversely affect the fluid that is transported through the channel. A highly distributed potential effect causes less stress to be placed on the fluid as it moves through each individual channel. Reducing stress can be important when the fluid is delicate or has a morphology that should not be altered. This can be an important consideration if the transported fluid is, for example, blood, colloidal fluids, and other non-homogeneous liquid mixtures or suspensions.

Additionally, a highly distributed potential effect also enables less stress to be placed on items that come in contact with the channel inlets or outlets. For example, if the inventive active fluid transport device is configured in the form of a catheter connected to a vacuum source, the use of the microstructured discrete flow channels can allow the potential from the vacuum to be so highly distributed that minimal stress is placed on the bodily tissue that is exposed to the potential at the channel inlets. The active fluid transport device thus can allow a fluid to be removed from a body cavity while minimizing damage to nearby tissues.

The microchanneled configuration of the inventive active fluid transport device also is advantageous in that it allows each individual channel to readily fill with fluid from the ambient environment. And the discrete channel system allows channels to fill or remain void independent of one another. One channel can, for example, be completely filled with a liquid while its neighboring channel contains only air. In conventional fluid transport devices, the channels are much larger and/or are not discrete and therefore often contain a two-phase flow of both liquid and air. The inventions promotion of single-phase flow for liquids also beneficially reduces the stress on the liquid passing through the device and can minimize noise pollution. The invention thus is advantageous in that it is capable of safely and quietly transporting a liquid from one site to another.

Also, the use of small flow channels in a structured surface allows the device to resist relatively high impact and compression forces, bending angles, and vacuums without collapse of the flow channels. This advantage enables the active fluid transport device to be used in situations where such forces might be present, for example, under heavy objects or on the floor where persons walk or during orthoscopic surgical procedures where fluid is used to keep the surgical site inflated and visually unimpaired but often requires a flexible fluid extraction means that is subject to compression or high angle bending that would otherwise pinch off conventional tubing.

GLOSSARY

In describing the present invention, the following terms are defined as set forth below:

"Aspect ratio" is the ratio of a channel's length to its hydraulic radius;

"Connector" means any mechanism, e.g. an apparatus, device, or combination of parts, that is configured to allow application of a potential from a potential source along discrete microstructured flow channels;

"Capillary module" is a device that possesses discrete microstructured flow channels that have channel inlets and channel outlets;

"Discrete flow channels" are channels that are capable of independently accommodating a potential to direct a fluid along a particular channel substantially independent of adjacent channels;

"Hydraulic radius" is the wettable cross-sectional area of a channel divided by the length of its wettable perimeter. For a circular channel, the hydraulic radius is one-fourth its diameter;

"Flexible" means capable of being bent or flexed without significant flow channel constriction;

"Fluid" means a volume of gas and/or liquid;

"Microreplication" or "microreplicated" means the production of a microstructured surface through a process where the structured surface features retain an individual feature fidelity during manufacture, from product-to-product, that varies no more than about 50 $\mu$m;

"Microstructured channels" or "microstructured flow channels" is used in this document to refer to channels that have a minimum aspect ratio of about 10:1 and a hydraulic radius no greater than about 300 $\mu$m;

"Polymeric material" means a material that is formed by combining monomers to produce a natural or synthetic organic molecule(s) that contains one or more repeating units regularly or irregularly arranged in the organic molecule(s);

"Potential" means energy that is capable of moving a fluid;

"Potential source" or "source that provides a potential" means any entity that is capable of supplying energy for doing work that can move a fluid; and "Structured surface" means a nonplanar surface that has defined features in a predetermined arrangement.

BRIEF DESCRIPTION OF THE DRAWINGS

FIG. 4a is partial cross-sectional view of the liquid recovery device 40 of FIG. 4 taken along line 4a—4a;

DETAILED DESCRIPTION OF PREFERRED EMBODIMENTS

In the Figures, like components are labeled with like numerals throughout the several illustrations.

Figure 1:
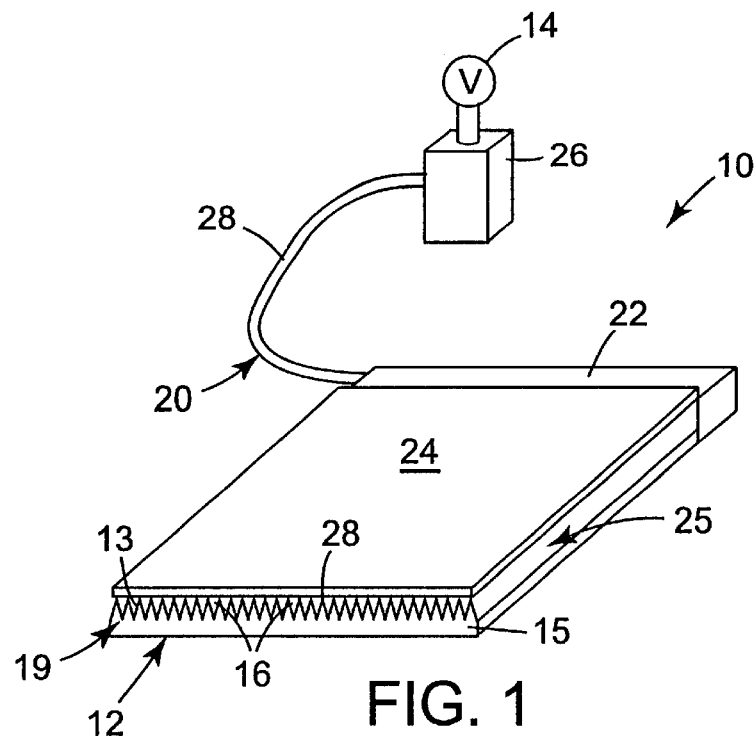
FIG. 1 is a perspective view of an active fluid transport device 10 in accordance with the invention having a structured layer 12 combined with a cap layer 24 to provide multiple discrete channels 16 that are in communication with a vacuum source 14.

In FIG. 1 an active fluid transport device 10 is illustrated which basically includes a layer 12 of polymeric material that has a structured surface 13 on one of its two major surfaces. The device 10 also includes a source 14 for providing a potential to assist in moving a fluid over the structured surface 13 of the active fluid transport device 10. Layer 12 also includes a body layer 15 from which the structured surface 13 projects. Body layer 15 serves to support structured surface 13 to retain the individual structured features together in layer 12.

Layer 12 may be comprised of flexible, semi-rigid, or rigid material, which may be chosen depending on the particular application of the active fluid transport device 10. The layer 12 comprises a polymeric material because such materials can be accurately formed to create a microstructured surface 13. Substantial versatility is available because polymeric materials possess many different properties suitable for various needs. Polymeric materials may be chosen, for example, based on flexibility, rigidity, permeability, etc. The use of a polymeric layer 12 also allows a structured surface to be consistently manufactured to produce a large number of and high density of channels that when capped form discrete fluid flow channels 16. Thus, a highly distributed fluid transport system can be provided that is amenable to being manufactured at a high level of accuracy and economy. The structured polymeric surface 13 may be made from the same or different materials of the body layer 15.

Figure 2A:
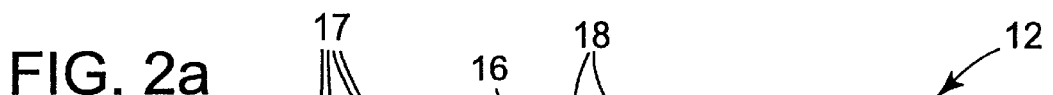
FIG. 2a through 2c are end views of structured layers 12, 12b, 12c, illustrating possible channel configurations that may be used in an active transport device in accordance with the present invention.

As shown in FIG. 2a, channels 16 can be defined within the layer 12 in accordance with the illustrated embodiment by a series of v-shaped sidewalls 17 and peaks 18. In some cases, the sidewalls 17 and peaks 18 may extend entirely from one edge of the layer 12 to another without alteration—although, in some applications, it may be desirable to shorten the sidewalls 17 and thus extend the peaks 18 only along a portion of the structured surface 13. That is, channels 16 that are defined between peaks 18 may extend entirely from one edge to another edge of the layer 12, or such channels 16 may only be defined to extend over a portion of the layer 12. Channels that extend only over a portion may begin at an edge of the layer 12, or they may begin and end intermediately within the structured surface 13 of the layer 12. The channels are defined in a predetermined, preferably ordered arrangement over a continuous surface of polymeric material.

As shown in FIG. 1, each of the channels 16 is opened at one edge of the layer 12 to define channel inlets 19. Fluid can thus pass through the inlets 19 guided by the channels 16 toward a further edge of the layer 12 to a connector 20.

The connector 20 preferably is in fluid communication with each of the channels 16 through outlets (not shown) and also is in fluid communication with the potential source 14. The connector 20 may be fashioned in a variety of forms but as illustrated in FIG. 1, it includes a manifold 22. Manifold 22 is provided with a plenum (not shown) that is defined internally therein and which is in fluid communication with channels 16. The plenum may simply comprise a chamber within the manifold 22 that is sealingly connected to at least a plurality of the channels 16. The manifold 22 may be flexible, semi-rigid, or rigid, like the layer 12. A second manifold (not shown) also may be provided at the side of layer 12 having inlets 20 so as to supply fluid to the channel 16, depending on the particular application.

In accordance with the invention, the connector may take on essentially any adaptation that enables the potential to be transferred from the source to the multiple channels. Although a manifold with a plenum and a tubing have been described, other connectors—such as compression couplings, or seals and gaskets that fluidically join a conduit to the flow channels and permit the isolation or partition of regions of higher and lower potential from the surrounding environment—are contemplated for use in this invention. The connector could also include capillary fibers, for example, less than 10 µm in inner diameter, each in fluid communication with an individual channel to allow individual fluids to flow discretely through separate channels. The connector could also be a molded chamber(s), a microstructured fluid conduit integrally or nonintegrally disposed relative to the discrete flow channels, or for example, a system or mechanism that allows the discrete microstructured flow channels to be seated in a centrifuge or that allows a flow stream such as a jet to be directed at channel inlets or outlets.

To close off or enclose at least a plurality of the channels 16 at the peaks 18, a cap layer 24 may be juxtaposed against the structured surface. Cap layer 24 thus closes at least a plurality of the channels to create discrete flow channels 16 in a capillary module 25. The capillary module typically would have a thickness of 1 to 10 millimeters (mm), more typically 2 to 6 mm. Cap layer 24 may likewise sealingly connect to the manifold 22 so that plural discrete channels 16 provide active fluid transport channels based upon the creation of a potential difference across the channels 16 from a first potential to a second potential. Cap layer 24 typically has a thickness of about 0.01 to 1 mm, more typically 0.02 to 0.5 mm. If the channels of the invention are hermetically sealed then the flexible system of channels could generally withstand high pressure without rupture, as a result of the hoop strength of the small individual channels.

The cap layer 24 may be bonded to the peaks 18 of some or all of the structured surface 13 to enhance creation of discrete channels 16. This can be done thermally or by using conventional adhesives that are compatible with the cap layer material 24 and the polymeric structured layer 12. Formation of discrete channels 16 may be accomplished through heat bonding, ultrasonic welding, compression, or mechanical engagement such as an interference fit. Bonds may be provided entirely along the peaks 18 to the cap layer 20, or the bonds may be spot welds or bonds that may be placed thereon in an ordered or random pattern.

Cap layer 24 preferably is made from a polymeric material such as the polymers described below for the structured polymeric layer. Polymers may be chosen such that the cap layer can be secured to the structured surface 13 without using an adhesive. Such a polymer could be chosen such that the cap layer becomes securely welded to the structured surface by applying heat, for example, as from an ultrasonic welding operation.

The potential source may comprise essentially any means capable of establishing a potential difference along a plurality of the flow channels 16 to encourage fluid movement from a first location to a second location. The potential is sufficient to cause, or assist in causing, fluid flow through plural flow channels 16, which is based in part on the fluid characteristics of any particular application. As shown in FIG. 1, the potential source 14 may comprise a vacuum generator (V) that is conventionally or otherwise connected to a collector receptacle 26. The collector receptacle 26 is fluidically connected to the manifold 18 by way of a conventional flexible tube 28. Thus, fluid can be drawn from outside the capillary module 25 into the inlets 19, through channels 16, through manifold 22, through tube 28, and into the collection receptacle 26. The receptacle 26 may advantageously be openable to empty its contents or may be otherwise connected to conventional drainage systems.

In the case where the potential source 14 comprises a vacuum generator (V), the vacuum provided to the channels 16 via manifold 22 can be sufficient to adequately seal the cap layer 24 to the peaks 18. That is, the vacuum itself will hold the cap layer 24 against peaks 18 to form discrete channels 16. Preferably, each of the channels 16 that are defined by the structured surface 13 is closed off by the cap layer 24 so as to define a maximum number of discrete channels 16 capable of independently accommodating the potential. Fluid crossover between channels 16 may be effectively minimized, and the potential provided from an external source can be more effectively and efficiently distributed over the structured surface 13 of layer 12.

Connection between a microstructure-bearing surface, or capillary module, to a fluid conveyance or potential source can be achieved through an affixed manifold or manifolds as required. Multiple potential sources may also be employed depending on the particular adaptation or application. Pressure differential is an efficient fluid motivation method or potential that may be used to drive flow across the microstructure-bearing surface(s). Pressure differential can be established readily through use of a pumping system and applied either in the form of positive or negative pressure.

Other potential sources 14 may be used in the present invention instead of or in conjunction with a vacuum generation device (V). Essentially any man-made manner of causing or encouraging fluid flow through the channels 16, particularly liquid flow, is contemplated for using this invention. The potential source is separate from the channeled structure and/or capillary module, or in other words is not intrinsic to the channeled structure and/or capillary module. That is, the invention does not rely solely on the properties of the channeled structure to cause fluid movement, for example, by capillary action. Examples of other potential sources include but are not limited to, vacuum pumps, pressure pumps and pressure systems such as a fan, magneto hydrodynamic drives, acoustic flow systems, centrifugal spinning, hydrostatic heads, and any other known or later developed fluid drive system utilizing the creation of a potential difference that causes or encourages fluid flow to at least some degree. Additionally, any applied field force that acts directly on the fluid such as a centrifugal force or magnetic field that causes fluid to move within the channels of the invention may be considered a fluid motive potential. The invention does not, however, contemplate gravity as being a potential source that is applied along the flow channels unless it is so employed by way of a connector, such as a conduit in fluid communication with a volume of liquid, for example, a hydrostatic head that drives liquid into the device by gravity. Fluid may also be caused to flow through channels by the action of a siphon where atmospheric pressure creates the potential to move fluid in the channels.

Figure 2B:
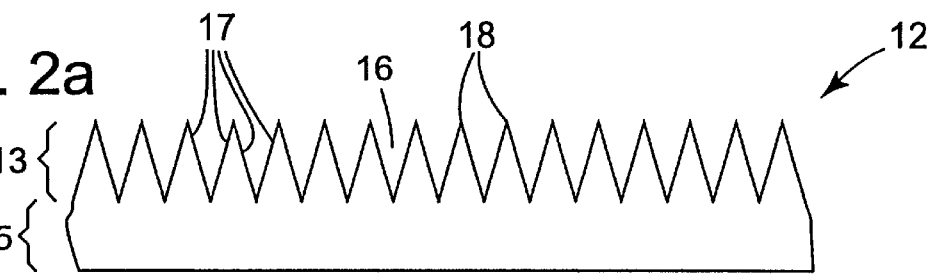

Although the fluid transport device shown in FIG. 1 has a structured surface comprising multiple v-shaped peaks 18 (as shown in FIG. 2a), other configurations are contemplated. For example, as shown in FIG. 2b, channels 16' have a wider flat valley between slightly flattened peaks 18'. Like the FIG. 2a embodiment, a cap layer can be secured along one or more of the peaks 18' to define discrete channels 16'. In this case, bottom surfaces 30 extend between channel sidewalls 31, whereas in the FIG. 2a embodiment, sidewalls 17 connect together along lines.

Figure 2C:
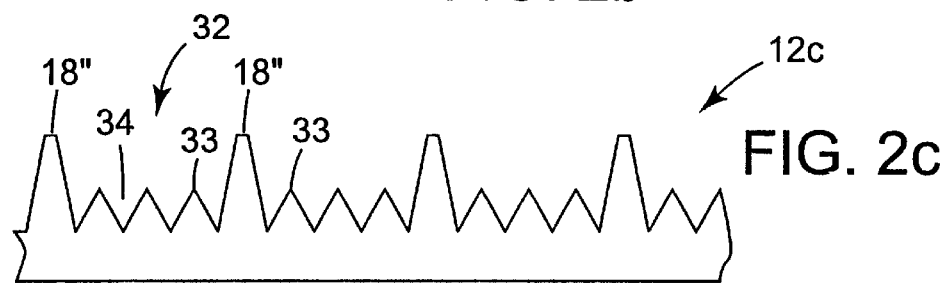

FIG. 2c illustrates a configuration where wide channels 32 are defined between peaks 18", but instead of providing a flat surface between channel sidewalls, a plurality of smaller peaks 33 are located between the sidewalls of the peaks 18". These smaller peaks 33 thus define secondary channels 34 therebetween. Peaks 33 may or may not rise to the same level as peaks 18", and as illustrated create a first wide channel 32 including smaller channels 34 distributed therein. The peaks 18" and 33 need not be evenly distributed with respect to themselves or each other. The smaller channels 34 may be used to control fluid flow through the wider channels 32 by modifying frictional forces along the channel's length.

Although FIGS. 1 and 2a–2c illustrate elongated, linearly-configured channels, the channels may be provided in other configurations. For example, the channels could have varying cross-sectional widths along the channel length—that is, the channels could diverge and/or converge along the length of the channel. The channel sidewalls could also be contoured rather than being straight in the direction of extension of the channel, or in the channel height. Generally, any channel configuration that can provide at least multiple discrete channel portions that extend from a first point to a second point within the fluid transport device are contemplated. The channels may be configured to remain discrete along their whole length if desired.

Figure 3A:
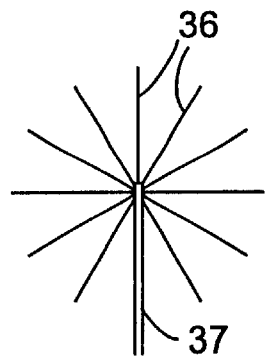
FIGS. 3a and 3b are top schematic views of structured layers illustrating alternative channel structures that may be used in an active transport device in accordance with the present invention.
Figure 3B:
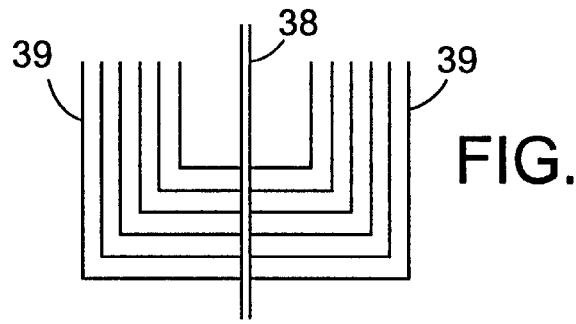

FIGS. 3a and 3b schematically illustrate channel configurations in plan view that may define a structured surface in an active fluid transport device of the invention. As shown, plural discrete non-parallel converging channels 36 provide for intermediate collection of fluid. These converging channels 36 connect to a single discrete channel 37. This minimizes the provision of outlet ports to one. As shown in FIG. 3b, a central channel 38 connects to a plurality of channel branches 39 that may be designed to cover a particular area for similar reasons. Again, generally any pattern is contemplated in accordance with the present invention as long as a plurality of discrete channels are provided over a portion of the structured surface from a first point to a second point. Like the above embodiments, the patterned channels shown in FIGS. 3a and 3b are preferably covered with a cap layer for further defining discrete flow channels that allow the potential to be accommodated along a particular channel essentially independent of its neighboring channels.

As to any of the channels contemplated above and in accordance with the present invention, such channels are defined within a structured layer by the structured surface of a first major surface of the layer. The channels in accordance with the present invention are configured to be discrete to allow any one channel to receive fluid from the ambient environment independently of the other channels. The microstructured size of each channel encourages single-phase flow of fluid in bulk volumes. Without having air entrained in the liquid, noise generation is significantly reduced and less stress can be placed on liquids that are transported through the active fluid transport device.

The individual flow channels of the microstructured surfaces of the invention are substantially discrete. That is, fluid can move through the channels independent of fluid in adjacent channels. The channels independently accommodate the potential relative to one another to direct a fluid along or through a particular channel independent of adjacent channels. Preferably, fluid that enters one flow channel does not, to any significant degree, enter an adjacent channel, although there may be some diffusion between adjacent channels. It is important to effectively maintain the discreteness of the micro-channels in order to effectively transport the fluid and maintain advantages that such channels provide. Not all of the channels, however, may need to be discrete for all embodiments. Some channels may be discrete while others are not. Additionally, channel "discreteness" may be a temporary phenomenon driven, for example, by fluctuating pressures.

In U.S. Pat. application Ser. No. 09/099,565, an active fluid transport device is disclosed which uses uncapped microstructured flow channels that become capped when the device is placed on a surface having a mating profile (e.g., flat structured channeled surface placed on a flat surface). The patent application was filed on the same day as this application and is entitled *Fluid Guide Device Having An Open Structured Surface For Attachment To A Fluid Transport Source*.

The structured surface is a microstructured surface that defines discrete flow channels that have a minimum aspect ratio (length/hydraulic radius) of 10:1, in some embodiments exceeding approximately 100:1, and in other embodiments at least about 1000:1. At the top end, the aspect ratio could be indefinitely high but generally would be less than about 1,000,000:1. The hydraulic radius of a channel is no greater than about 300 $\mu$m. In many embodiments, it can be less than 100 $\mu$m, and may be less than 10 $\mu$m. Although smaller is generally better for many applications (and the hydraulic radius could be submicron in size), the hydraulic radius typically would not be less than I Jim for most embodiments. As more fully described below, channels defined within these parameters can provide efficient bulk fluid transport through an active fluid transport device.

The structured surface can also be provided with a very low profile. Thus, active fluid transport devices are contemplated where the structured polymeric layer has a thickness of less than 5000 micrometers, and possibly less than 1500 micrometers. To do this, the channels may be defined by peaks that have a height of approximately 5 to 1200 micrometers and that have a peak distance of about 10 to 2000 micrometers.

Microstructured surfaces in accordance with the present invention provide flow systems in which the volume of the system is highly distributed. That is, the fluid volume that passes through such flow systems is distributed over a large area. Microstructure channel density from about 10 per lineal cm (25/in) and up to 1,000 per lineal cm (2500/in) (measured across the channels) provide for high fluid transport rates. Generally, when a common manifold is employed, each individual channel has an aspect ratio that is at least 400 percent greater, and more preferably is at least 900 percent greater than a manifold that is disposed at the channel inlets and outlets. This significant increase in aspect ratio distributes the potential's effect to contribute to the noted benefits of the invention.

Figure 4:
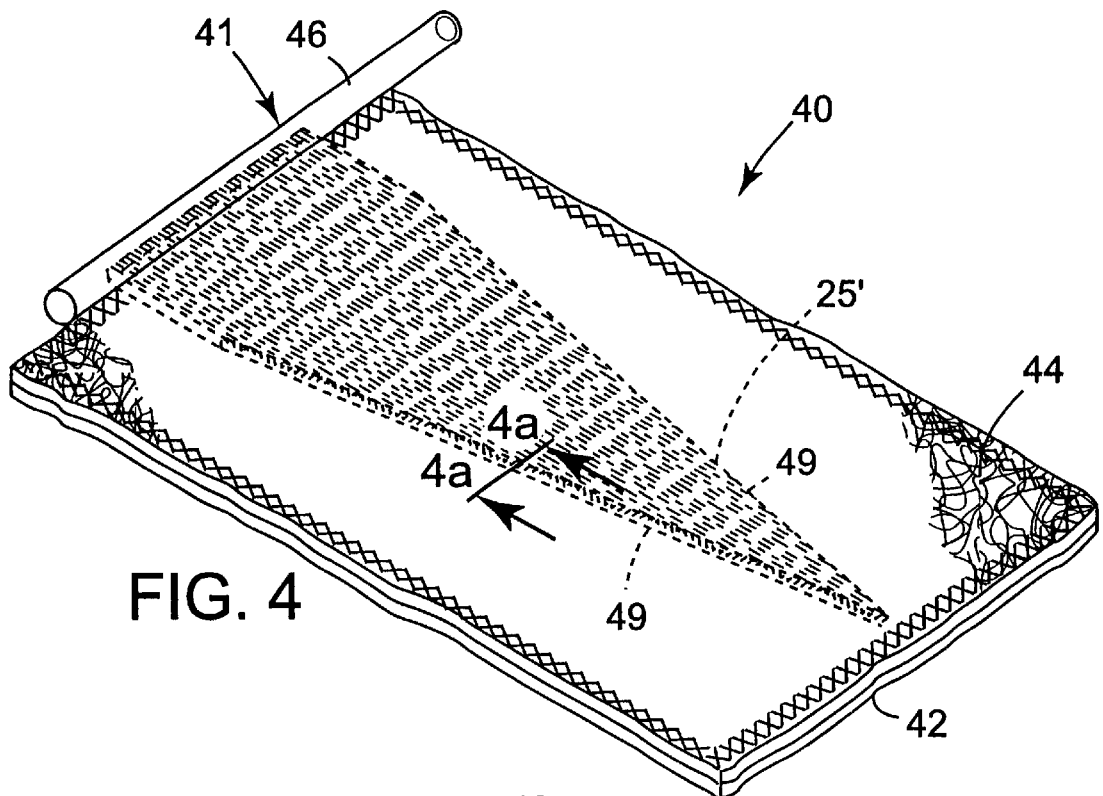
FIG. 4 is a perspective view of a liquid recovery device 40 in accordance with the present invention.

FIG. 4 shows a liquid acquisition and evacuation mat 40 that incorporates an active fluid transport device similar to device 10 described above in FIG. 1. The liquid acquisition and evacuation mat 40 can include a capillary module 25' that is similar to the module 25 of FIG. 1 but is in a pennant configuration and is sandwiched between a support layer 42 and a liquid sorbing layer 44. The liquid absorbing layer 44 is disposed above the capillary module 25' when the mat 40 is in use, to act as a collector or reservoir for liquid, and it permits liquid that contacts the layer to travel through it. The liquid sorbing layer 44 can comprise essentially any material that is capable of permitting these functions, such as non-woven webs, particularly those containing meltblown microfibers and microfiber microwebs. An example of a suitable web material is disclosed in U.S. Pat. No. 4,813,948 to Insley. The support layer 42 not only provides structural support and integrity to the liquid acquisition and evacuation mat 40, but it defines a bottom surface that is preferably impermeable to the liquid to be collected. Thus, liquid can be collected and held within the liquid sorbing layer 44 and be prevented from passing through the support layer 42. The capillary module 25' includes a connector such as a manifold 46 that is preferably sealingly connected to a potential source, such as a vacuum generator.

Figure 4A:
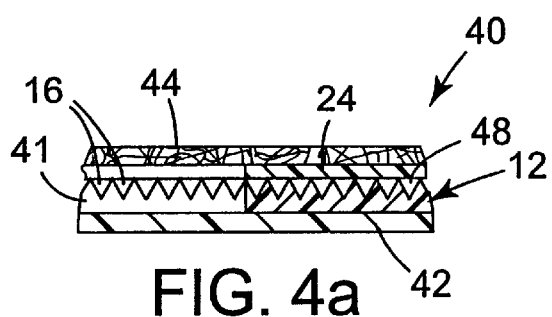

The capillary module 25' is preferably shaped to expose inlets 48 at various locations throughout the length of the liquid evacuation mat 40. One way to do this is to provide the capillary module 25' with angled edges 49 that converge from a point near manifold 46 toward an opposed edge of the liquid extraction mat 40. The use of angled edges 49 enlarges the cross-sectional area of each inlet 48. FIG. 4a shows a portion of an edge 49 where inlets 48 for various channels are enlarged. The inlets 48 are open within the structure of the liquid extraction mat 40, preferably along substantially the entire length of the liquid extraction mat 40 and also at various transverse widths throughout. Other shaped edges can be provided to accomplish similar or different results. It may be desirable, for example, to concentrate a collection of inlets at particular area of a mat product that is likely to require greater fluid recovery. Also, plural capillary modules 25' may be incorporated within a single liquid evacuation mat 40. The plural capillary modules 25' may be provided from the same side or different sides of the liquid evacuation mat 40 with each connected to separate manifolds or a common manifold.

By constructing the liquid acquisition and evacuation mat 40 that has a capillary module 25' sandwiched between a liquid sorbing layer 44 and a support layer 42, a majority of the fluid holding capacity of the mat 40 can be provided where the liquid sorbing layer 44 is directly over the support layer 42 without the capillary module 25' therebetween. That is, with a cap layer 24 (which may be fluid impermeable) incorporated within the active fluid transport device 41, fluid will have a tendency to flow into the lower areas surrounding the device 41. By withdrawing fluid at the inlets 48 and through any number of the independent channels of the active fluid transport device 41, fluid can be efficiently removed from substantially the entire surface of the liquid evacuation mat 40.

The mat 40 also could be constructed such that the support layer 42 is a microchanneled structural surface like layer 12. Support layer 42 also could be eliminated, and structured layer 12 could be sized such that it extends beyond capillary module 25' and preferably at least beneath the whole surface (or beneath a substantial portion) of liquid sorbing layer 44.

In such an embodiment, the extended structural layer 12 would act as the support layer that prevents fluids from passing beneath the mat 40. The extended structural layer could be integral with layer 12. What is meant by "integral" is that the support layer and the structured layer 12 are one-and-the-same, i.e., manufactured at the same time and not produced separately and then joined together. The channels in such a support layer could be dendritically configured as shown in FIGS. 3a and 3b to encourage fluid movement from the out extremities of the extended layer 12 into the capillary module 25'.

The use of microstructured channels in accordance with the present invention, enables the fluid to be removed by the active fluid transport device 41 without generating substantial noise. As indicated above, this is primarily because the microstructured channels facilitate single-phase flow of fluid through each of the independent channels with minimized air/liquid mixing and turbulence. The single phase flow may operate as plug flow or as continuous single-phase flow through the channels.

A liquid extraction and evacuation mat such as the one described may find application in areas where fluid discharges are present and require removal. Such applications might include removal of fluid from floors and equipment in surgical areas, surgical drapes, bed pads, and in smaller configurations in personal care devices, such as incontinent diapers and pads. The extraction mat could also be used in industrial applications to remove oils and other liquids that leak or otherwise fall from machinery.

Many configurations of the capillary module could be designed to deliver desired performance. Multiple layers of linear microstructures could be employed to increase throughput per unit width of module. Modules with end-manifolds could be constructed to provide channel inlets that are exposed on an interior boundary of a structured layer rather than at the periphery or exterior boundary as shown in the figures. Channel inlets could be exposed on a structured layer by cutting out an interior section of layer. This would expose channel inlets that are both directly connected to a potential source, such as a vacuum, and those openings that are connected to the source via an end manifold and directly connected channels.

A device that is similarly constructed but has a selectively permeable separation media covering the microstructured flow channels is described in U.S. patent application Ser. No. 09/100,163, filed on the same day as this patent application and entitled *Microstructured Separation Device*.

Figure 5:
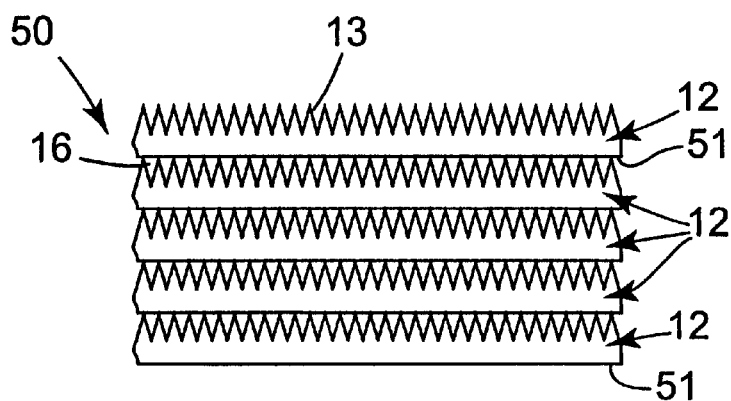
FIG. 5 is an end view of a stack 50 of structured layers 12 that are disposed upon one another so that bottom major surfaces 51 of the layers 12 close off the structured surface 13 of a lower layer to define multiple discrete channels 16.

As shown in FIG. 5, a plurality of layers 12, each having a microstructured surface 13 can be constructed to form a stack 50. This construction clearly multiplies the ability of the structure to transport fluid because each layer significantly increases flow capacity. The layers may comprise different channel configurations and/or number of channels, depending on a particular application. Furthermore, this type of stacked construction can be particularly suitable for applications that are restricted in width and therefore require a relatively narrow fluid transport device from which a certain fluid transfer capacity is desired. Thus, a narrow device can be made having increased flow capacity.

A significant advantage of the stack 50 is that a second major surface 51 of layers 12 (the surface facing opposite the structured surface 13) can close off or cap the channels of an adjacent layer 12. In other words, separate cap layers are not required, although they may be utilized, particularly to cover the exposed microstructured surface 13 of the uppermost layer. Separate cap layers, however, could be disposed over the second major surface 51 as an additional layer. The material chosen for such an additional layer could be a polymeric material or otherwise depending on the particular application. The layers in the stack may be bonded to one another in any number of conventional ways as descried above, or they may simply be stacked upon one another such that the structural integrity of the stack can adequately define discrete flow channels. This ability may be enhanced, as described above, when a vacuum is utilized as the potential source. The second major surface 51 may be planar as shown, or it may be a structured surface similar to or different from surface 13.

Although the device shown in FIG. 5 includes a stack of 5 structured surfaces 12, stacks may be configured that have other numbers of stacks, for example, greater than 10 or even greater that 100 structured layers, and may include tributary stacks that converge into a larger stack. For example, the five-layered stack shown in FIG. 5 could be divided into quarters, and each of the four tributary stacks (which possess channel inlets) could converge into the larger stacked configuration as shown in FIG. 5 which in turn could be attached to a connector that communicates with a potential source. The stack could include multiple connectors to allow multiple potential sources of varying potential to be attached to as subsets in the stack.

Stacked microstructured channels may also be used as filtration media as described in U.S. patent application Ser. No. 09/106,506, filed on the same day as this patent application and entitled *Structured Surface Filtration Media*.

Figure 6:
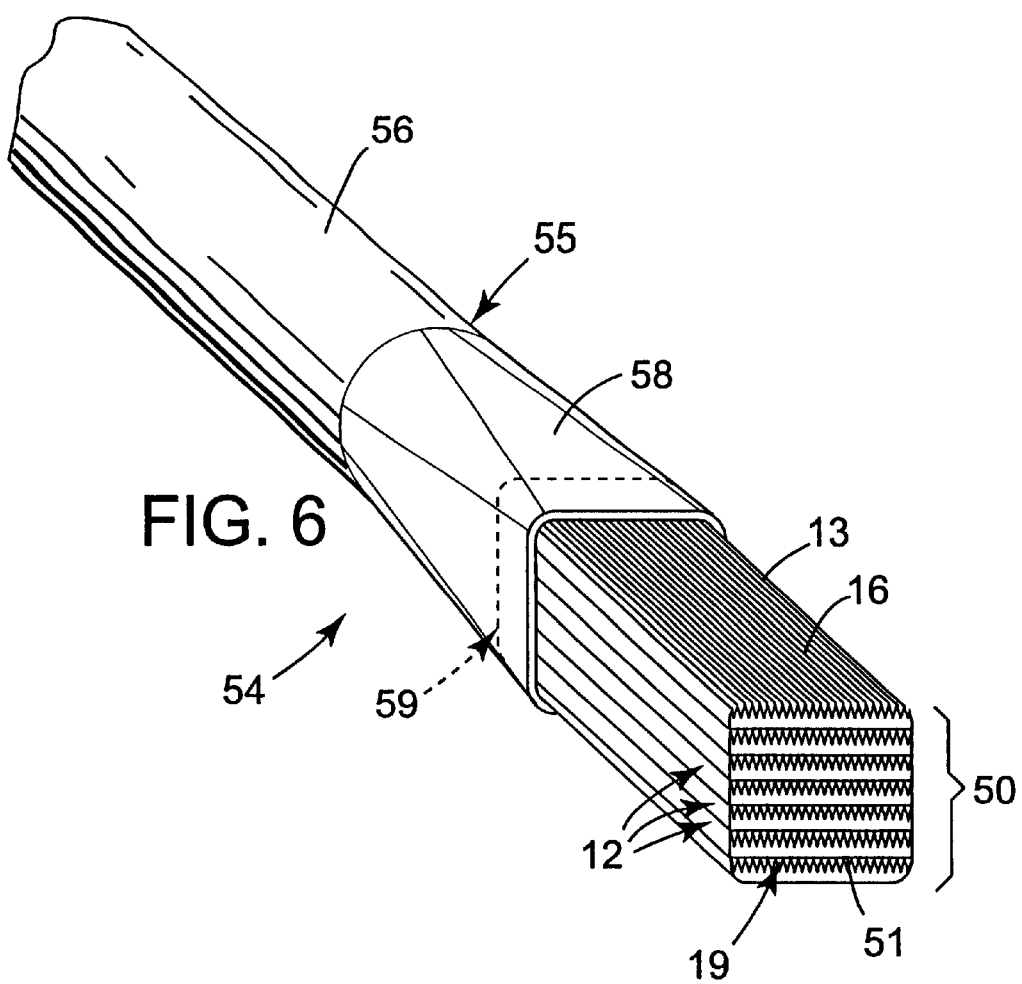
FIG. 6 is a perspective view of an aspirator 54 in accordance with the present invention utilizing a stack 50 of multiple microstructured layers 12.

In FIG. 6, a stacked construction, such as shown in FIG. 5, is used in an aspirator 54. The aspirator 54 employs a stack 50 that comprises a plurality of layers 12, each having a microstructured polymeric surface 13 over one major surface thereof The second major surface 51 of layers 12 acts as a cap layer, closing the channels 16 of the adjacent sub layer 12 to create a stack or capillary module 50 having a multiplicity of channel inlets 19 at the aspirator tip or end. The second major surface 51 may be polymeric, or it may be covered with other materials, e.g. metal foils, etc., as desired.

The capillary module 50 can be joined to a connector 55 that includes a tubing 56 and an adapter 58. The tubing 56 may be fastened or otherwise joined to a potential source, such as a vacuum. The adapter 58 joins the square cross-sectional capillary module 50 to the round cross-sectional tubing 56 at the sealing connection region 59. The adapter 58 may be conventionally, sealingly connected to tubing 56 and to the module 50 by adhesive or other bonding techniques. The stack or module 50 may or may not be further enclosed by a conduit or tubing. Alternatively, the tubing 56 and module 50 can be connected together by a section of heat shrink tubing into which ends of the tubing 56 and the module 50 are inserted before shrinking. The layers 12, and thus the stack 50, may extend only a short distance from the adapter 58 so as to provide a relatively stiff aspirator end, or the layers 12 may extend further to make the aspirator 54 more flexible. To provide a flexible and conformable aspirator end, the individual layers 12 preferably are not bonded or otherwise secured to each other over the whole surface of the layer, particularly at the end, to allow the layers 12 to slide or move relative to one another in the longitudinal direction of the channels 12. This independent sliding motion enables the tip to be bent around an axis normal to the flow channels 16. When used in an aspirator, the module typically would be about 1 to 10 cm in length. A stiff aspirator may be more applicable for insertion into tight spaces, while flexibility may be desired so that the aspirator tip can be positioned at a more distal location while conforming to a path to that location.

A sheath could also be applied over the capillary module 50 as described. Dependent on the application, a porous or closed sheath could be placed around the stack. A porous sheath could be used for applications where the sheath acts as a sieve or filter, and a closed sheath construction might be particularly suited to applications in endoscopic surgical procedures where liquid fluid delivery or extraction is needed.

An active fluid transport device could also be employed as a smoke or gas evacuator. The flexible aspirator, for example, could be used in applications where smoke plumes from laser surgery might be encountered. It could also be used to recover methane gases and permeating fluids or gases from landfills, acting as a geosynthetic membrane.

Preferably, the layers 12 are not adhered to one another, although they may connected as such if needed. Where the layers 12 are not bonded together, the integrity of the stack 50, and/or a vacuum applied through tubing 56 can be relied upon to adequately define independent flow channels 16. In accordance with the present invention, the microstructured surface 13 of the layers 12 define flow channels 16 that promote single-phase liquid flow. This is again advantageous in that noise is reduced, which is particularly beneficial in the medical field.

Another advantage of the aspirator 54, which comprises a stack of individual layers 12 that are unattached to one another, is that the stack 50 may be divided and even further subdivided into a plurality of aspirator branches. That is, a part of the stack 50 may be directed to one particular location where fluid X is to be extracted, while another portion of the stack 50 is directed to another area where fluid Y is extracted. Particularly, where the aspirator 54 relies on a vacuum supplied through conduit or tubing 56 to remove fluid, any number of such divisions can be made whereby a plurality of individual discrete flow channels are provided within each branch. Tubing 56 could also be subdivided so that fluid from each particular branch or subdivision in stack 50 is directed to its own respective conduit to allow appropriate fluid flow. Simultaneous irrigation and/or aspiration could be achieved by such a device. That is, the separate conduits could be adopted to transport an irrigation fluid and an aspirated fluid. This feature may be particularly beneficial for medical uses, including dental uses, for aspirating more than one spot at a time.

A stacked module construction may include plural stacks arranged next to one another. That is, a stack such as shown in FIG. 5 may be arranged adjacent to a similar or different stack. Then, they can be collected together by an adapter, such as shown in FIG. 6, or they may be individually attached to a fluid transfer tubing or the like.

Although the aspirator shown in FIG. 6 has essentially a linear profile, it may be desirable in some embodiments to use an aspirator that has a different configuration. For example, the tubing 56 or the adapter 58 and/or the stack 50 may be curved or curvable to allow the aspirator to reach difficult areas or to allow the aspirator to support itself For example, if the aspirator shown in FIG. 6 could be used by a dentist to withdraw saliva and aqueous rinsing fluids that are present in the patient's mouth. If the aspirator was hooked at its end, it could rest on the patient's lip. The tubing 56 or adaptor 58 desirably is flexible to achieve such a curved configuration and may be made of a dead soft material, or may contain such a material, to enable the aspirator to be temporarily bent into such a curved configuration. Such a device would be highly beneficial in that the dentist could more easily communicate with the patient and vice versa without having to overcome the noise that is associated with conventional dental aspirators.

Other features or items may also be provided in front of the inlets 19 to the channels 16 for added functions. For example, a soft fibrous end may be placed on the aspirator tip by adhering a mass of cotton gauze or sponge-like material. This feature may be particularly useful for dental or other medical applications. Features could also be added on the channel outlet side of the module to provide, for example, an irrigation function in conjunction with or in lieu of an aspirator.

Current aspirator technologies generally utilize relatively larger diameter tubes to acquire and convey the aspirated liquid. It is not uncommon for these tubes to have an inner diameter of one centimeter or larger. Unless the tubes are completely flooded during use, which is not typical, the aspirator functions primarily in two-phase flow with air being the continuous phase that motivates the liquid movement in the flow system. This requires a relatively large air-to-liquid ratio, one in which the momentum of the flowing air is sufficient to carry the liquid. The required momentum of the air flow has many negative effects on the function of typical medical aspirators. These negative effects may include trauma to tissues contacted at the aspirator tip, damage to aspirated blood cells due to shearing and aeration, high volumetric air flows that can cause atomization of potential biohazardous liquids, increasing occupational exposure, and the general noise level of their operation.

Figure 7:
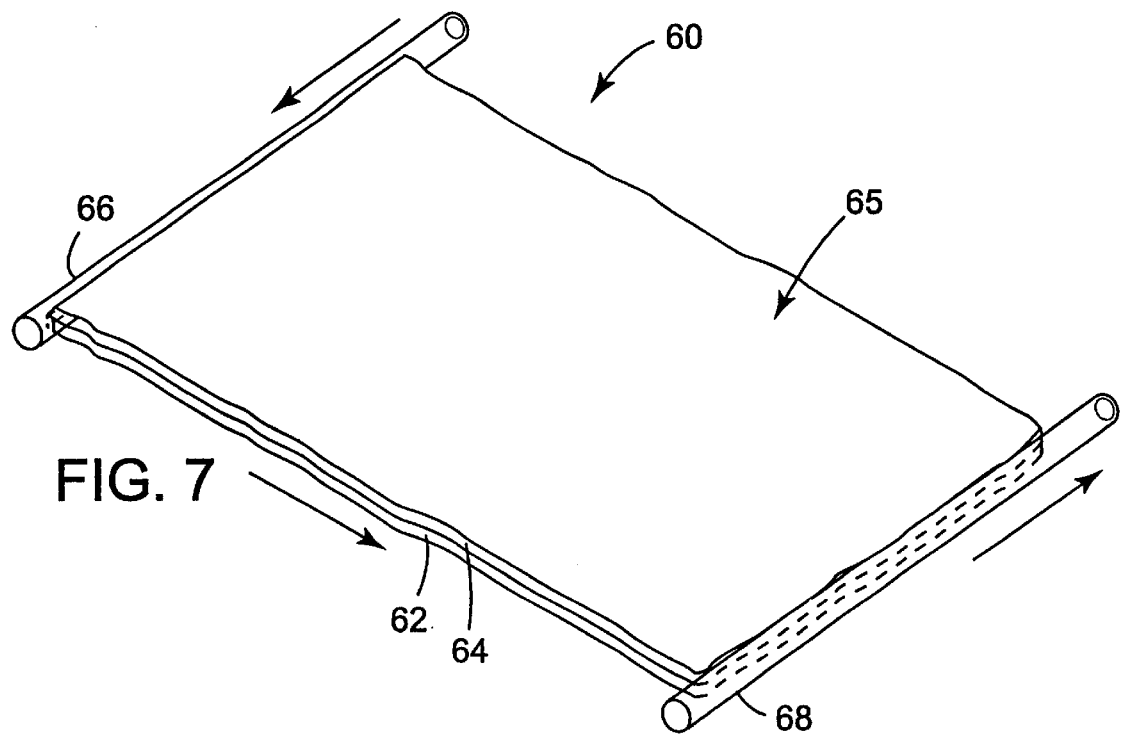
FIG. 7 is a perspective view of another active fluid transport device 60 in accordance with the present invention which has a microstructured layer 62 covered with a cap layer 64 to define multiple discrete channels (not shown) that are connected between a first manifold 66 and a second manifold 68.

FIG. 7 illustrates yet another embodiment of an active fluid transport device 60 in accordance with the present invention. Device 60 may comprise a construction similar to the device 10 shown in FIG. 1. That is, it may include a layer 62 that has a microstructured surface on one of its major surfaces and that has at least a plurality of channels that are covered with a cap layer 64 to form a capillary module 65. The cap layer 64 could have thickness dimensions described above in reference to FIG. 1. To permit good heat transfer characteristics, the cap layer 64 preferably has a thickness of about 0.02 to 0.2 mm. The capillary module also could have the dimensions described above in reference to FIG. 1. The channels (not shown) are preferably arranged so that inlets (not shown) are in fluidic communication with an inlet manifold 66, while at another edge of the device 60, an outlet manifold 68 can be fluidically connected to the channel outlets (not shown). The potential source may be connected to the transport device 60 by way of the inlet manifold 66 or the outlet manifold 68 depending on how fluid is intended to move through the device. For example, a pump (not shown) could be employed to move fluid from the inlet manifold 66 to the outlet manifold 68 by fluidically joining the pump to the inlet manifold via a connector that would include manifold 66. Alternatively, a vacuum could be placed in fluid communication with the outlet manifold 68 via a connector that includes that manifold.

Active fluid transport device 60 may be particularly useful where it is desirable to circulate a particular fluid through the device 60 to influence a characteristic of the fluid by its contact with layers 62 or 64. That is, the fluid may be treated by its passing through the channels defined by the layers 62 and 64. Fluid treatment might include chemical, catalytic, and ionization reactions promoted by constituents placed on or in the channel surfaces. Separation treatments such as by sorption of fluid constituents onto properly prepared channel surfaces would be effective due to the high ratio of channel surface area to channel volume. The same attributes could be used to permit the sensing or detecting of a passing fluid where the contact layers 62 or 64 act as the fluid interface component in a sensor or detector system. A fluid detection system might monitor fluid conductivity, pH, temperature, or composition. Alternately, a fluid influenced by the surrounding environment as it circulates through the channels could be monitored as part of a detection system where the device 60 would itself function as and element in a sensor or detection system. The surface of the flow channels could be functionalized to respond or detect these physical conditions. Heating or cooling could be used to thermally treat the fluid. A microstructured channeled active fluid heat exchanger is disclosed in U.S. patent application Ser. No. 09/099,632, filed on the same day as this patent application and entitled *Microchanneled Active Fluid Heat Exchanger.* Fluid streams of different composition also could be made to merge together to interact and treat one another as a means to cause a reaction, dilution, or blending. Otherwise, the fluid may change a characteristic of either or both of layers 62 or 64, such as, for example, a heat exchanger. An observation, detection, or analytical device such as a microscope or spectrometer, remote to layers 62 or 64, may be used to analyze fluid as it passes in a thin film through the channels. In any case, as with any of the noted embodiments, the structure can be made from flexible, semi-rigid, or rigid materials.

With flexible materials, the mechanically flexible nature of such a device would allow it to be used in contoured configurations. Flexible devices may be relatively large so that they can be easily handled without breakage and to provide a highly distributed fluid flow over a large area that needs to be affected by the device. A flexible fluid transport device can take the form of a blanket, for example, for cooling or heating a patient. Such a flexible device can be conformable to an object, or may be conformable along with an object (e.g. provided on a cushion). Although the fluid transport device can be flexible, it can also demonstrate resistance to collapse from loads and kinks. The microstructured nature of the capillary module 65 provides sufficient structure that can be utilized within any active fluid transport device to impart load-bearing integrity to support, for example, a standing person. The small size of the flow channels, as well as their geometry, enable relatively high forces (for example, exceeding 10 kPa or even greater than 50 kPa) to be applied to the surface without collapsing the flow channels.

Figure 8:
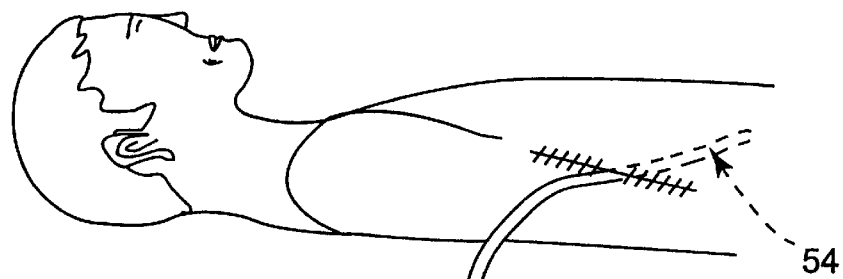
FIG. 8 illustrates a use of the aspirator 54 shown in FIG. 6 on a patient.

FIG. 8 shows the aspirator 54 used on a patient and connected to a collection receptacle 57. In this case, the collection receptacle 57 can be connected to a potential source, such as a small vacuum pump. An aspirator shown in FIG. 8 could be used to remove bodily fluids such as blood, plasma, or bodily secretions from a surgical site, or surgical irrigation fluids such as buffered saline solutions, sterile solutions, etc.

Figure 9:
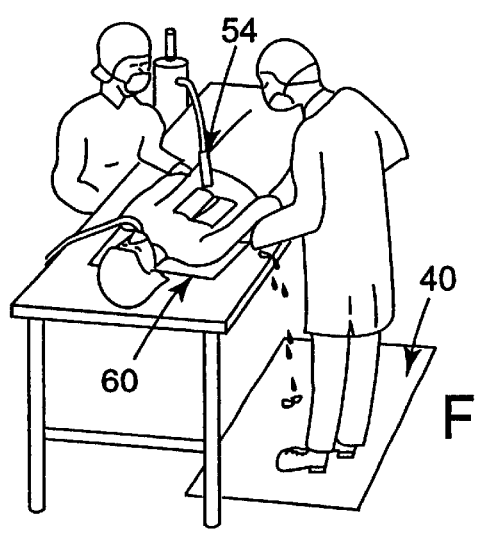
FIG. 9 shows multiple uses of active fluid transport devices 40, 54, and 60 in an operating room.

FIG. 9 shows examples of multiple specific uses of active fluid transport devices in accordance with the present invention. In the medical field, a liquid acquisition and evacuation mat 40 can be positioned where spillage is likely to occur to absorb and remove the spilled fluid. The removal operation may be continuous or intermittent, depending on the need. The recovered fluid could be bodily fluids or medical irrigation fluids. An aspirator 54, as described above, is also shown for usage during a medical procedure to remove, for example, bodily fluids, while the patient is shown positioned on a device 60 that may be in the form of a flexible blanket for affecting the patient with, for example, heating or cooling.

Heat transport devices, such as device 60 depicted in FIGS. 7 and 9, possess some benefits. Because the heat transfer fluid is maintained in very small channels, there is minimal fluid stagnation in the channels. Fluids in laminar flow in channels exhibit a velocity flow profile where the fluid at the channel's center has the greatest velocity. Fluid at the channel boundary in such flow regimes is essentially stagnate. Depending on the size of a channel, the thermal conductivity of the fluid, and the amount of time a fluid spends moving down the channel, this flow profile can create a significant temperature gradient across the channel. In contrast, channels that have a minimum aspect ratio and a hydraulic radius in accordance with the invention will display a smaller temperature gradient across the channel because of the small heat transfer distance. A smaller temperature gradient is advantageous as the fluid will experience a uniform heat load as it passes through the channel.

Residence time of the heat transfer fluid throughout the system of small channels also can be essentially uniform from inlet manifold 66 to outlet manifold 68. A uniform residence time is beneficial because it minimizes non-uniformity in the heat load a fluid experiences.

The reduction in temperature gradient and the expression of a uniform residence time also contribute to overall efficiency and, for a given rate of heat transfer, allow for smaller temperature differentials between the heat transfer fluid and the element to be heated or cooled. The smaller temperature differentials reduce the chance for local hot or cold zones that would be undesirable when the heat exchanger is used in thermally sensitive applications such as skin or tissue contact. The high contact surface area, per unit volume of heat transfer fluid, within the heat transfer module increases the system's volumetric efficiency.

The heat transport device may also be particularly useful in confined areas. The material economics of a microstructure-bearing film based unit would make them appropriate for limited or single use applications, such as in medical devices, where disposal is required to address contamination concerns.

A heat transport device of the invention is beneficial in that it can be flexible, allowing its use in various applications. The device can be contoured around tight bends or curves. The flexibility allows the devices to be used in situations that require intimate contact to irregular surfaces. The inventive fluid transport devices, including the heat exchanger, may be fashioned to be so flexible that the devices or capillary modules can be conformed about a mandrel that has a diameter of approximately one inch (2.54 cm) or greater without significantly constricting the flow channels or the structured polymeric layer. The inventive devices also could be fashioned from polymeric materials that allow the fluid transport device to be non-detrimentally conformed about a mandrel that is approximately 1 cm in diameter.

The making of structured surfaces, and in particular microstructured surfaces, on a polymeric layer such as a polymeric film are disclosed in U.S. Pat. Nos. 5,069,403 and 5,133,516, both to Marentic et al. Structured layers may also be continuously microreplicated using the principles or steps described in U.S. Pat. No. 5,691,846 to Benson, Jr. et al. Other patents that describe microstructured surfaces include U.S. Pat. Nos. 5,514,120 to Johnston et al., 5,158,557 to Noreen et al., 5,175,030 to Lu et al., and 4,668,558 to Barber.

Structured polymeric layers produced in accordance with such techniques can be microreplicated. The provision of microreplicated structured layers is beneficial because the surfaces can be mass produced without substantial variation from product-to-product and without using relatively complicated processing techniques. The microreplicated surfaces preferably are produced such that the structured surface features retain an individual feature fidelity during manufacture, from product-to-product, which varies no more than 25 $\mu$m.

Fluid transport layers for any of the embodiments in accordance with the present invention can be formed from a variety of polymers or copolymers including thermoplastic, thermoset, and curable polymers. As used here, thermoplastic, as differentiated from thermoset, refers to a polymer which softens and melts when exposed to heat and re-solidifies when cooled and can be melted and solidified through many cycles. A thermoset polymer, on the other hand, irreversibly solidifies when heated and cooled. A cured polymer system, in which polymer chains are interconnected or crosslinked, can be formed at room temperature through use of chemical agents or ionizing irradiation.

Polymers useful in forming a structured layer in articles of the invention include but are not limited to polyolefins such as polyethylene and polyethylene copolymers, polypropylene, ethylene/vinyl acetate polymers, ethylene/ethyl acrylate polymers. Other useful polymeric materials include vinyl polymers (e.g., polyvinyl chloride, polyvinyl alcohol, vinyl chloride/vinyl alcohol copolymers, polyvinylidene chloride, polyvinylidine diflouride (PVDF)), acrylate polymers (e.g., polymethyl methacrylate), polycarbonate polymers, polyesters (e.g., polyethylene terephthalate), polyamides (e.g., Nylon), polyurethanes, polysaccharides (e.g. cellulose acetate), polystyrenes (e.g., polystyrene/methyl methacrylate copolymer), polysiloxane polymers (e.g., polysiloxane and organopolysiloxane polymers). Fluid transport members can be cast from curable resin materials (monomer and prepolymer mixtures) such as acrylates or epoxies and cured through free radical polymerization pathways promoted chemically, by exposure to heat, UV, gamma or electron beam radiation. Plasticisers, fillers or extenders, antioxidants, ultraviolet light stabilizers, surfactants, and the like may be utilized within the polymers of the invention.

As indicated above, there are applications where flexible active fluid transport devices are desired. Flexibility may be imparted to a structured polymeric layer using polymers described in U.S. Pat. Nos. 5,450,235 to Smith et al. and 5,691,846 to Benson, Jr. et al. The whole polymeric layer need not be made from a flexible polymeric material. The body layer (15, FIG. 1), for example, could comprise a flexible polymer, whereas the structured portion or portion could comprise a more rigid polymer. The patents cited in this paragraph describe use of polymers in this fashion to produce flexible products that have microstructured surfaces. The body layer also could conceivably be made from materials other than polymers if desired.

Polymeric materials including polymer blends can be modified through melt blending of plasticizing active agents such as surfactants or antimicrobial agents. Surface modification of the structured surfaces can be accomplished through vapor deposition or covalent grafting of functional moieties using ionizing radiation. Methods and techniques for graft-polymerization of monomers onto polypropylene, for example, by ionizing radiation are disclosed in US Pat. Nos. 4,950,549 and 5,078,925. The polymers may also contain additives that impart various properties into the polymeric structured layer. For example, plasticizers can be added to decrease elastic modulus to improve flexibility.

Active transport of fluids, both gasses and liquids, is central to many unit operations. These operations can include, for example, heat transfer, mass transfer, ion exchange, and reactive chemistry. Additionally, the present invention provides an apparatus and method for active thin film reaction in applications such as chemical or radiant reactors. In a chemical reactor, a chemical or catalytic agent might similarly be supported on a microstructured surface or on an interfacing surface. In a radiant reactor, some form of radiation could be transmitted through a surface to cause an effect on the fluid being transferred.

Preferred embodiments of the invention may use thin flexible polymer films that have parallel linear topographies as the microstructure-bearing element. For purposes of this invention, a "film" is considered to be a thin (less than 5 mm thick) generally flexible sheet of polymeric material. The economic value in using inexpensive films with highly defined microstructure-bearing film surfaces is great. Flexible films can be used in combination with a wide range of capping materials and can be used unsupported or in conjunction with a supporting body where desired. The capillary modules formed from such microstructured surfaces and caps may be flexible for many applications but also may be associated with a rigid structural body where applications warrant. For example, when using the microstructured surface to aspirate fluid, it may be desirable to affix the module to a rigid body that serves as a handle. The structured surface has independent channels that may each expressed over a continuous surface region to allow independent fluid movement between the independently structured channels.

Because the active fluid transport devices of the invention include microstructured channels, the devices commonly employ a multitude of channels per device. As shown in some of the embodiments illustrated above, inventive active fluid transport devices can easily possess more than 10 or 100 channels per device. Some applications, the active fluid transport device may have more than 1,000 or 10,000 channels per device. The more channels that are connected to an individual potential source allow the potential's effect to be more highly distributed. For a device such as an aspirator, the potential that is commonly employed ranges from about 20 to about 40 kPa, and more commonly from about 40 to about 60 kPa.

The inventive active fluid transport devices of the invention may have as many as 10,000 channel inlets per square centimeter of cross section area. Active fluid transport devices of the invention may have at least approximately 50 channel inlets per square centimeter. Typical devices can have about 1,000 channel inlets per $cm^2$. By having so many channel inlets per unit cross sectioned area, the effect of the potential is so highly distributed at that location of the active fluid transport device, that negligible forces may be imparted onto objects that come in contact with the channel inlet area.

EXAMPLES

Example 1—Liquid Acquisition and Evacuation Mat

A vacuum assisted liquid collection apparatus was constructed using a capillary module formed from a polymeric layer that contained microstructured channels that were capped with a flat film. The apparatus resembled the device shown in FIG. 4. To complete the apparatus, a nonwoven absorbent was placed above the capillary module, and the module was attached to a vacuum source.

The capillary module was formed by laminating the microstructured channel bearing polymeric layer to a single layer of Scotch Pack™ type 29905 film. The microstructure-bearing layer was formed by casting a molten polymer onto a nickel tool that had microstructured channels on one surface. The polymer used to form the structured layer was low density polyethylene, Tenite™ 1550P from Eastman Chemical Company. This polymer has a secant modulus of $193 \times 10^6$ Pascals as determined by ASTM D 790. A nonionic surfactant, Triton X-102 from Rohm & Haas Company, was melt blended into the base polymer to increase the surface energy of the structured layer. The channels were formed in the continuous length of the cast polymer. The nickel casting tool was produced by shaping a smooth copper surface with diamond scoring tools to produce the desired structure, followed by an electroless nickel plating step to form a nickel tool. The tool used to form the polymeric layer was fashioned to produce a microstructured "V" channel like those illustrated in FIG. 2a. The channels formed had a nominal depth of 459 $\mu$m an a opening width of 420 $\mu$m. This resulted in a channel that had a hydraulic radius of 62.5 $\mu$m when capped. The dimensions of both the structured polymer layer and the cap layer were 40×10 centimeters (cm). The linear microstructure of the microstructure-bearing layer was parallel to the long axis of the laminate. The polymeric layer and cap layer were juxtaposed such that the microstructured channels faced towards the low melting Scotch Pack™ film.

The structured layer and cap layer were then fused together by heat welding. The heat welds were approximately 5 millimeters (mm) wide and were disposed parallel to the long axis of the lamination on the outside edges only. Construction of the capillary module was completed by cutting one end of the welded lamination into a chevron pattern, thus exposing capillary openings along the long axis of the module.

The apparatus was assembled by sandwiching the capillary module between a layer of nonwoven sorbent and a thin liquid impermeable film. The blown microfiber absorbent was prepared as described in U.S. Pat. No. 4,813,948 to Insley and was comprised of a source web of polypropylene (Fina 400 MFI) microfibers (60 wt %) with fibers in the 5 to 10 $\mu$m diameter size combined with 15 denier PET staple fibers (20 wt %), and microfiber microwebs (20 wt %). A non-ionic surfactant type OP9, available from Henkel of Charlotte, N.C., was melt blended with the resin in all the microfiber elements during extrusion at a fiber add-on rate of 10 wt % to render the fibers instantaneously wettable with water. The weight and solidity of the resulting web was 180 grams per square meter ($g/m^2$) and 6% respectively. The bulk absorbency of the web was 2,000 $cm^3/m^2$. The support layer was a 0.02 millimeter (mm) film (75 wt % PP/25 wt % EVA, Dow Chemical). The sorbent web and the support layers were held together using a hot melt spray adhesive. The adhesive (HL-1358-X ZP, H.B. Fuller, St. Paul, Minn.) was applied to the absorbent at a rate of 10 $g/m^2$. The capillary module was positioned within the structure such that only a small portion of the module extended beyond the absorbent and the support layer. The chevron end of the module was aligned with the center of the absorbent sheet.

A manifold was then fitted over the extended end of the capillary module. The manifold was formed by placing a cut in the side wall of a tubing section, VI grade 3.18 mm inner diameter, 1.6 mm wall thickness tubing from Nalge Co. of Rochester, N.Y. The slit was cut with a razor in a straight line along the tube axis. The slit length was approximately the same as the capillary module width. The tube was then fitted over the end of the capillary module and hot melt glued in place. One open end of the tube, at the capillary module, was sealed closed with hot melt adhesive.

Fluid evacuation capability of the apparatus was evaluated by saturating the absorbent and attaching the capillary module to a vacuum source via the tubing. The test unit, with sorbent side facing up, was placed in a pan situated on top of a top-loading balance. After a vacuum of 28 mm mercury (Hg) was applied to the unit, the amount of water in the pad was recorded and the extraction rate of the liquid was determined. Extraction rate results are shown below in Table 1:

TABLE 1

| Saturation Level (%) | Instantaneous Extraction Rate (ml/min) |
| --- | --- |
| 100% | 950 |
| 77% | 400 |
| 68% | 180 |
| 62% | 138 |
| 57% | 108 |
| 53% | 78 |
| 50% | 72 |
| 39% | 40 |
| 33% | 20 |

As demonstrated, the apparatus was effective in acquiring and removing liquid from the point of discharge. The test unit was particularly suited in managing fluids at high saturation or flooded level and able to extract fluid at a rate close to a liter per minute. The unit was able to accept multiple fluid charges and operated in an essentially silent mode. There was only a relatively small volume of air entrained with the extracted fluid as was observed in the aspiration bottle. The liquid acquisition and evacuation mat was durable and flexible and had the ability to drape and conform to the surface contours onto which it was placed and could be bent over a sharp contour without compromising the capillary structure. The microstructured surface of the capillary module was mechanically durable and was able to withstand the weight of an individual (about 25 kPa) standing, or, seated on stool with casters rolling over, the module without collapse.

Example 2—Medical Aspiration Device

A vacuum assisted aspiration apparatus similar to the aspiration shown in FIG. 6 was constructed using a stack of polymeric microstructured channel layers resembling the stack shown in FIG. 5. The stack was made by layering together strips of the microstructured channel-bearing layer of Example I in such a fashion that the microstructure of one film layer faced the smooth back side of the adjacent layer to create a capillary module. The linear channeled structure of the microstructured polymeric layer was oriented parallel to the long axis of the stack. The dimension of the individual structured polymeric layers was 5 mm×115 mm. Ten structured polymeric layers were used to form the capillary module. A manifold was affixed to one end of the stack to facilitate a vacuum attachment. The manifold was formed from heat activated shrink tubing that was placed over the end of the stack and an abutting tube like used in Example 1. The shrink tubing FP-301-¼" (available from 3M Company, St. Paul, Minn.) was then heat activated around both the attachment tube and stack.

To test the acquisition and conveyance capacity of the unit, a 25 milliliter (ml) graduated cylinder was filled with water and was evacuated. After attaching a vacuum source of 28 mm Hg to the manifold of the capillary module, the tip of the aspirator was allowed to contact and extend below the liquid surface approximately 5 mm. The aspirator tip was moved down from the surface as the column receded. The time required to evacuate the graduated cylinder was seven seconds, resulting in an average extraction rate of 214 ml/min.

Because of the small channels in the aspiration unit, little air was entrained with the acquired liquid. This is an important distinction relative to known aspirator technologies.

The example unit carried approximately 200 individual channels, each channel having an aspect ratio of 1840 to 1 and a hydraulic radius of 62.5 μm. The small channels of capillary modules were easily flooded with aspirated fluid and therefore did not operate in a two-phase flow regime to carry fluid.

With a low pressure drop applied over the aspirated module the unit could be employed as a cannula or surgical drain. Operating with flooded capillaries rather than open tubes, the unit would minimize the possibility of back flow of air into the body cavity.

All of the patents and patent applications cited above are incorporated by reference into this document in total.

What is claimed is:

1. An active fluid transport device that comprises:
  (a) a layer of polymeric film material having a first major surface that includes a structured surface that has a plurality of discrete flow channels disposed thereon, the flow channels extend from a first point to a second point along the structured surface and have a minimum aspect ratio of about 10:1 and a hydraulic radius no greater than about 300 micrometers;
  (b) a source external to the structured surface for providing a potential over the flow channels; and
  (c) a connector that is in fluid communication between the discrete flow channels and the external source, which connector allows the potential from the source external to the structured surface to be applied to the flow channels to promote fluid movement through the flow channels from a first location to a second location.

2. The active fluid transport device of claim 1, wherein the layer of polymeric material is microreplicated.

3. The active fluid transport device of claim 1, wherein the connector includes a manifold that has a plenum defined internally therein.

4. The active fluid transport device of claim 1, wherein the connector includes a manifold that is disposed fluidically between the flow channels and the potential source, the potential from the potential source being applied to the flow channels via the manifold.

5. The active fluid transport device of claim 1, wherein the connector includes one or more of the following: a manifold, a compression coupling, seal, or gasket that fluidically joins a conduit to the flow channels, capillary fibers, a microstructured fluid conduit, a system for seating the discrete microstructured flow channels in a centrifuge, and a system for allowing a flow stream to be directed at channel inlets or channel outlets.

6. The active fluid transport device of claim 1, wherein the flow channels include a cap layer that is juxtaposed against the structured surface.

7. The active fluid transport device of claim 6, wherein the cap layer is sealingly secured to the structure surface to define the discrete flow channels.

8. The active fluid transport device of claim 1, wherein the potential source includes one or more of the following: a vacuum generator, a pump, a fan, a magneto-hydrodynamic drive, an acoustic flow system, a centrifuge, and a hydrostatic head.

9. The active fluid transport device of claim 1, wherein the structured surface includes v-shaped channels.

10. The active fluid transport device of claim 1, wherein the flow channels are configured to have a flat valley between slightly flattened peaks.

11. The active fluid transport device of claim 1, wherein the structured surface includes a plurality of channels that have smaller channels disposed therebetween.

12. The active fluid transport device of claim 1, wherein the flow channels include plural discrete converging channels that connect to a larger discrete channel.

13. The active fluid transport device of claim 1, wherein the flow channels have a minimum aspect ratio exceeding 100:1.

14. The active fluid transport device of claim 1, wherein the flow channels have a minimum aspect ratio of at least 1,000:1.

15. The active fluid transport device of claim 13, wherein the aspect ratio is less than 1,000,000:1.

16. The active fluid transport device of claim 1, wherein the hydraulic radius is no greater than 100 micrometers.

17. The active fluid transport device of claim 1, wherein the hydraulic radius is less than 10 micrometers.

18. The active fluid transport device of claim 1, wherein the layer of polymeric material has a thickness less than 5,000 micrometers.

19. The active fluid transport device of claim 1, wherein the layer of polymeric material has a thickness less than 15,000 micrometers.

20. The active fluid transport device of claim 1, wherein the flow channels are defined by peaks that have a height of approximately 5 to 1,200 micrometers and that have a peak distance of about 10 to 2,000 micrometers.

21. The active fluid transport device of claim 1, wherein the microstructure channel density is from about 10 per lineal centimeter up to 1,000 per lineal centimeter.

22. The active fluid transport device of claim 3, wherein the flow channels have an aspect ratio that is at least 400% greater than the manifold.

23. The active fluid transport device of claim 3, wherein the flow channels have an aspect ratio that is at least 900% greater than the manifold.

24. A liquid acquisition and evacuation mat that comprises the active fluid transport device of claim 1, and further includes a liquid absorbing layer that is disposed above the layer of polymeric material when the mat is in use, the liquid absorbing layer permitting liquid that contacts the layer to travel therethrough.

25. The liquid acquisition and evacuation mat of claim 24, wherein the liquid absorbing layer comprises a nonwoven web of meltblown microfibers.

26. The liquid acquisition and evacuation mat of claim 24, further comprising a support layer that is disposed beneath the liquid absorbing layer when the mat is in use, the support layer being liquid impermeable.

27. The liquid acquisition and evacuation mat of claim 26, wherein the support layer includes a microstructured layer that has flow channels disposed thereon.

28. The liquid acquisition and evacuation mat of claim 27, wherein the support layer is an integral extension of the layer of polymeric material that is present in the active fluid transport device.

29. The liquid acquisition and evacuation mat of claim 24, that includes a capillary module that has a pennant configuration.

30. The active fluid transport device of claim 1, wherein the device includes multiple structured layers in the form of a stack.

31. The active fluid transport device of claim 30, wherein the layer of polymeric material has a second major surface that caps the structured surface on the first major surface.

32. The active fluid transport device of claim 30, wherein the stack includes at least 10 structured layers.

33. The active fluid transport device of claim 30, wherein the stack includes at least 100 structured layers.

34. An aspirator that comprises the active fluid transport device of claim 1.

35. An aspirator that comprises the stack of claim 30, as a capillary module.

36. The aspirator of claim 33, wherein the stack is flexible.

37. The aspirator of claim 36, wherein the stack is about 1 to 10 centimeters in length, and wherein the multiple structured layers are not secured to each other at the stack's inlet end.

38. The aspirator of claim 35, wherein a sheath is disposed over the stack of claim 35.

39. The aspirator of claim 35, wherein the connector includes a conduit that is attachable to a vacuum, the connector being fluidically attached to the flow channels in the stack.

40. The aspirator of claim 36, wherein the stack is subdivided into a plurality of branches.

41. The aspirator of claim 40, wherein a plurality of conduits are placed in fluid communication with the plurality of branches such that fluid is transported through some of the conduits independent of other conduits.

42. The aspirator of claim 41, wherein a first conduit is adapted to transport an irrigation fluid, and a second conduit is adapted to transport an aspirated fluid.

43. The aspirator of claim 30, being adaptable such that it can rest on a person's lip such that the aspirator can withdraw saliva and other fluids present in the person's mouth.

44. The active fluid transport device of claim 1, further comprising first and second manifolds disposed at the flow channels' inlets and outlets.

45. A heat exchanger that comprises the active fluid transport device of claim 41.

46. The heat exchanger of claim 43, wherein the heat exchanger is flexible.

47. A blanket that comprises the heat exchanger of claim 44.

48. The heat exchanger of claim 43, wherein the discrete flow channels include a cap layer that has a thickness of about 0.02 to 0.2 mm.

49. The active fluid transport device of claim 1, wherein the flow channels are adapted to influence a characteristic of a fluid that flows therethrough.

50. The active fluid transport device of claim 49, wherein the fluid is treated by chemical, catalytic, or ionization reactions promoted by constituents placed on or in the flow channel surfaces.

51. The active fluid transport device of claim 49, wherein the flow channels are adapted to provide a separation treatment such that a fluid passing therethrough has constituents removed from its flow stream.

52. The active fluid transport device of claim 1, wherein the flow channels are configured such that fluid streams of different compositions merge together to interact.

53. The active fluid transport device of claim 1, wherein the flow channels are defined by the structured surface and a cap layer that are joined together in the form of a capillary module that can be conformed about a mandrel that has a diameter of approximately 2.5 centimeters without significantly constricting the flow channels.

54. The active fluid transport device of claim 1, wherein the layer of polymeric material includes a body layer that comprises a polymer that is more flexible than the polymer that defines the structured surface.

55. The active fluid transport device of claim 1, wherein the layer of polymeric material is in the form of a film.

56. The active fluid transport device of claim 1, having more than 100 discrete flow channels.

57. The active fluid transport device of claim 1, having more than 1,000 discrete flow channels.

58. The active fluid transport device of claim 1, having more than 10,000 discrete flow channels.

59. The active fluid transport device of claim 1, having 50 to 10,000 channel inlets per square centimeter.

60. The active fluid transport device of claim 1, wherein the connector includes discrete conduits that each fluidically connect to individual discrete flow channels.

61. A method of transporting a fluid which comprises passing the fluid through the active fluid transport device of claim 1.

62. The method of claim 61, wherein the fluid includes a bodily fluid.

63. The method of claim 62, wherein the bodily fluid includes saliva.

64. The method of claim 61, wherein the bodily fluid includes blood, plasma, or bodily secretions.

65. The method of claim 61, wherein the fluid includes smoke.

66. The method of claim 61, wherein the fluid includes a liquid.

67. The method of claim 66, wherein the liquid is an aqueous liquid.

68. An active fluid transport device that comprises:
(a) a layer of polymeric film material having a first major surface that includes a structured surface that has a plurality of discrete flow channels disposed thereon, the flow channels extend from a first point to a second point along the structured surface and have a minimum aspect ratio of about 10:1 and a hydraulic radius no greater than about 300 micrometers;
(b) a source external to the layer of polymeric film material for providing a potential over the flow channels; and
(c) a manifold disposed fluidically between the plurality of flow channels and the external source to connect the flow channels to the source and to apply the potential to the plurality of flow channels to promote fluid movement through the flow channels from a first location to a second location.

69. The active fluid transport device of claim 68, wherein the layer of polymeric material is microreplicated.

70. The active fluid transport device of claim 68, wherein the flow channels include a cap layer that is juxtaposed against the structured surface.

71. The active fluid transport device of claim 70, wherein the cap layer is sealingly secured to the structure surface to define the discrete flow channels.

72. The active fluid transport device of claim 68, wherein the potential source includes one or more of the following: a vacuum generator, a pump, a fan, a magneto-hydrodynamic drive, an acoustic flow system, a centrifuge, and a hydrostatic head.

73. The active fluid transport device of claim 68, wherein the structured surface includes v-shaped channels.

74. The active fluid transport device of claim 68, wherein the flow channels have a minimum aspect ratio exceeding 100:1.

75. The active fluid transport device of claim 68, wherein the flow channels have a minimum aspect ratio of at least 1,000:1 and a hydraulic radius no greater than 100 micrometers.

76. The active fluid transport device of claim 68, wherein the channels are discrete along their whole length.

77. The active fluid transport device of claim 68, wherein the hydraulic radius is less than 10 micrometers, and wherein the layer of polymeric material has a thickness less than 5,000 micrometers.

78. The active fluid transport device of claim 68, wherein the layer of polymeric material has a second major surface that includes a structured surface.

79. The active fluid transport device of claim 78, wherein the second major surface comprises a polymeric material.

80. A liquid acquisition and evacuation mat that comprises the active fluid transport device of claim 68, and further includes a liquid absorbing layer that is disposed above the layer of polymeric material when the mat is in use, the liquid absorbing layer permitting liquid that contacts the layer to travel therethrough.

81. The active fluid transport device of claim 68, wherein the device includes multiple structured layers in the form of a stack, and wherein the layer of polymeric material has a second major surface that caps the structured surface on the first major surface.

82. The active fluid transport device of claim 81, wherein the stack includes multiple connectors to allow multiple potential sources to be attached to the stack.

83. The active fluid transport device of claim 81, wherein the stack includes at least 10 structured layers.

84. An aspirator the comprises the active fluid transport device of claim 68.

85. A method of transporting a fluid, which comprises passing methane gas through the aspirator of claim 84.

86. A method of transporting a fluid, which comprises passing blood, plasma, secretions, surgical irrigation fluids, or a combination thereof through the aspirator of claim 84.

87. A heat exchanger that comprises the active fluid transport device of claim 68.

88. The active fluid transport device of claim 68, having more than 100 discrete flow channels.

89. The active fluid transport device of claim 68, having more than 1,000 discrete flow channels.

90. The active fluid transport device of claim 68, having 50 to 10,000 channel inlets per square centimeter.

91. The active fluid transport device of claim 68, further comprising a connector that includes discrete conduits that each fluidically connect to individual discrete flow channels.

92. A method of transporting a fluid which comprises passing a fluid through the active fluid transport device of claim 68.

93. The method of claim 92, wherein the fluid includes a bodily fluid.

94. The method of claim 92, wherein the bodily fluid includes saliva.

95. An active fluid transport device that comprises:
(a) a capillary module that includes a layer of polymeric film material that has a first major surface that includes a structured surface that is capped with a cap layer to define discrete flow channels, the discrete flow channels allow a fluid to be transported therethrough from a first point to a second point, the flow channels also have a minimum aspect ratio of 10:1 and a hydraulic radius no greater than about 300 miicrometers;
(b) a source external to the structured surface for providing a potential over the flow channels; and (c) a connector that is in fluid communication between the discrete flow channels and the external source, which connector allows the potential from the source external to the structured surface to be applied to the flow channels to promote fluid movement through the flow channels from a first location to a second location.

96. The active fluid transport device of claim 95, wherein the capillary module has a thickness of 1 to 10 millimeters.

97. The active fluid transport device of claim 95, wherein the capillary module has a thickness of 2 to 6 millimeters.

98. The active fluid transport device of claim 95, wherein the capillary module is flexible.

99. The active fluid transport device of claim 1, wherein the flow channels are defined by the structured surface and a cap layer that are joined together in the form of a capillary module that can be conformed about a mandrel that has a diameter of approximately 2.5 centimeters without significantly constricting the flow channels.

100. A method of transporting a fluid, which comprises:

transporting a fluid through the active fluid transport device of claim 95.

101. The active fluid transport device of claim 1, wherein the flow channels contain constituents that enable chemical, catalytic, and ionization reactions to occur as the fluid moves through the channels.

102. The active fluid transport device of claim 1, wherein the flow channels are adapted to detect physical characteristics of a fluid flowing therethrough.

103. A microstructured channeled device that comprises:

a layer of polymeric film material that has a first major surface that includes a structured surface;

the structured surface comprising flow channels that have a minimum aspect ratio of about 10:1 and a hydraulic radius no greater than about 300 micrometers;

the flow channels also possessing constituents that enable chemical, catalytic, and ionization reactions to occur as a fluid contacts the channels.

* * * * *

UNITED STATES PATENT AND TRADEMARK OFFICE
CERTIFICATE OF CORRECTION

PATENT NO.     : 6,290,685 B1                                             Page 1 of 1
DATED          : September 18, 2001
INVENTOR(S)    : Insley, Thomas I. et al.

It is certified that error appears in the above-identified patent and that said Letters Patent is hereby corrected as shown below:

Column 10,
Line 44, delete "I Jim" and insert in place thereof -- 1$\mu$m --.

Column 13,
Line 16, delete "that" and insert in place thereof -- than --.

Column 26,
Line 32, delete "the" and insert in place thereof -- that --.
Line 65, delete "miicrometers" and insert in place thereof -- micrometers --.

Signed and Sealed this

Second Day of September, 2003

JAMES E. ROGAN
*Director of the United States Patent and Trademark Office*